US011517593B2

(12) United States Patent
Lundgren Åkerlund et al.

(10) Patent No.: US 11,517,593 B2
(45) Date of Patent: Dec. 6, 2022

(54) PREVENTION AND TREATMENT OF BONE AND CARTILAGE DAMAGE OR DISEASE

(71) Applicant: Xintela AB, Lund (SE)

(72) Inventors: Evy Lundgren Åkerlund, Bjärred (SE); Christina Uvebrant, Malmö (SE); Jan Talts, Staffanstorp (SE)

(73) Assignee: Xintela AB, Lund (SE)

( * ) Notice: Subject to any disclaimer, the term of this patent is extended or adjusted under 35 U.S.C. 154(b) by 367 days.

(21) Appl. No.: 16/519,179

(22) Filed: Jul. 23, 2019

(65) Prior Publication Data

US 2020/0038449 A1 Feb. 6, 2020

Related U.S. Application Data

(63) Continuation of application No. PCT/EP2018/052104, filed on Jan. 29, 2018.

(60) Provisional application No. 62/451,372, filed on Jan. 27, 2017.

(51) Int. Cl.
| | | |
|---|---|---|
| *A61K 35/28* | (2015.01) | |
| *A61P 19/02* | (2006.01) | |
| *A61P 19/08* | (2006.01) | |
| *A61L 27/38* | (2006.01) | |
| *C07K 16/28* | (2006.01) | |
| *C12N 5/0775* | (2010.01) | |

(52) U.S. Cl.
CPC .......... *A61K 35/28* (2013.01); *A61L 27/3834* (2013.01); *A61L 27/3895* (2013.01); *A61P 19/02* (2018.01); *A61P 19/08* (2018.01); *C07K 16/2839* (2013.01); *C12N 5/0663* (2013.01); *C12N 5/0667* (2013.01); *A61L 2430/24* (2013.01)

(58) Field of Classification Search
None
See application file for complete search history.

(56) References Cited

FOREIGN PATENT DOCUMENTS

| WO | WO 01/80865 A2 | 11/2001 |
| WO | WO 01/080865 A3 | 11/2001 |
| WO | WO 03/106492 A1 | 12/2003 |
| WO | WO 2007/099337 A1 | 9/2007 |
| WO | WO 2008/072000 A2 | 6/2008 |

OTHER PUBLICATIONS

Steinert AF, Rackwitz L, Gilbert F, Nöth U, Tuan RS. Concise review: the clinical application of mesenchymal stem cells for musculoskeletal regeneration: current status and perspectives. Stem Cells Transl Med. 2012;1(3):237-247. (Year: 2012).*
Saeed H, Ahsan M, Saleem Z, Iqtedar M, Islam M, Danish Z, Khan AM. Mesenchymal stem cells (MSCs) as skeletal therapeutics—an update. J Biomed Sci. Apr. 16, 2016;23:41. (Year: 2016).*
Granero-Moltó F, Weis JA, Miga Ml, Landis B, Myers TJ, O'Rear L, Longobardi L, Jansen ED, Mortlock DP, Spagnoli A. Regenerative effects of transplanted mesenchymal stem cells in fracture healing. Stem Cells. Aug. 2009;27(8):1887-98. (Year: 2009 ).*
Leibacher J, Henschler R. Biodistribution, migration and homing of systemically applied mesenchymal stem/stromal cells. Stem Cell Res Ther. 2016;7:7. Published Jan. 11, 2016 (Year: 2016).*
Eggenhofer E, BenselerV, Kroemer A, et al. Mesenchymal stem cells are short-lived and do not migrate beyond the lungs after intravenous infusion. Front Immunol. 2012;3:297. Published Sep. 2, 20126. (Year: 2012).*
Ankrum JA, Ong JF, Karp JM. Mesenchymal stem cells: immune evasive, not immune privileged. Nat Biotechnol. Mar. 2014;32(3): 252-60. (Year: 2014).*
Li J, Ezzelarab MB, Cooper DK. Do mesenchymal stem cells function across species barriers? Relevance for xenotransplantation. Xenotransplantation. 2012;19(5):273-285. (Year: 2012).*
Kean TJ, Lin P, Caplan AI, Dennis JE. MSCs: Delivery Routes and Engraftment, Cell-Targeting Strategies, and Immune Modulation . Stem Cells Int. 2013;2013:732742. doi: 10.1155/2013/732742. Epub Aug. 13, 2013. (Year: 2013).*
Machado Cde V, Telles PD, Nascimento IL. Immunological characteristics of mesenchymal stem cells. Rev Bras Hematol Hemoter. 2013;35(1):62-67 (Year: 2013).*
Zhou X, von der Mark K, Henry S, Norton W, Adams H, de Crombrugghe B. Chondrocytes transdifferentiate into osteoblasts in endochondral bone during development, postnatal growth and fracture healing in mice. PLoS Genet. Dec. 4, 2014;10(12):e1004820. (Year: 2014).*
Abu-Hakmeh AE, Wan LQ. High-throughput cell aggregate culture for stem cell chondrogenesis. Methods Mol Biol. 2014;1202:11-9 . (Year: 2014).*
Acosta, F. L. Jr. et al., "The potential role of mesenchymal stem cell therapy for intervertebral disc degeneration: a critical overview", Neurosurgical Focus, vol. 19, No. 3, Sep. 2005.
Bartz, C. et al., "An ex vivo human cartilage repair model to evaluate the potency of a cartilage cell transplant", Journal of Translational Medicine, vol. 14:317, 2016.
Bocelli-Tyndall, C. et al., "Fibroblast growth factor 2 and platelet-derived growth factor, but not platelet lysate, induce proliferation-dependent, functional class II major histocompatibility complex antigen in human mesenchymal stem cells", Arthritis & Rheumatism, vol. 62, No. 12, pp. 3815-3825, 2010.
Bornes, T.D. et al., "Mesenchymal stem cells in the treatment of traumatic articular cartilage defects: a comprehensive review", Arthritis Research & Therapy, 16, pp. 432-451, 2014.
Burk, J. et al., "Growth and differentiation characteristics of equine mesenchymal stromal cells derived from different sources", The Veterinary Journal, 2012.
Camper, L. et al., "Isolation, Cloning, and Sequence Analysis of the Integrin Subunit a10, a β1-associated Collagen Binding integrin Expressed on Chondrocytes", Journal of Biological Chemistry, vol. 273, pp. 20383-20389, 1998.
Castañeda, S. et al., "Subchondral bone as a key target for osteoarthritis treatment", Biochemical Pharmacology, vol. 83, No. 3, pp. 315-323, 2012.

(Continued)

*Primary Examiner* — Marcia S Noble
(74) *Attorney, Agent, or Firm* — McNeill Baur PLLC

(57) ABSTRACT

Compositions and methods for the prevention and/or treatment of conditions involving disease or damage in mammalian cartilage and bone, using mesenchymal stem cells isolated with anti-integrin α10 antibodies are disclosed.

18 Claims, 16 Drawing Sheets

(56) References Cited

OTHER PUBLICATIONS

Dominici, M. et al., "Minimal criteria for defining muitipotent mesenchymal stromal cells. The International Society for Cellular Therapy position statement." Cytotherapy. 8, vol. 4, pp. 315-317, 2006.
Donahue, H. J. et al., "Joint diseases: from connexins to gap junctions", Nature Reviews Rheumatology, vol. 14, pp. 42-51, 2018.
English, K., "Mechanisms of mesenchymal stromal cell Immunomodulation", Immunology and Cell Biology, vol. 91, pp. 19-26, 2013.
Estes, B.T. et al., "Potent induction of chondrocytic differentiation of human adipose-derived adult stem cells by bone morphogenetic protein 6", Arthritis & Rheumatism, vol. 54, No. 4, pp. 1222-1232, 2006.
Fortier, L.A. et al., "Stem cells in veterinary medicine", Stem Cell Research and Therapy, vol. 2, No. 9, 2011.
Gelber, A. C., "Joint injury in young adults and risk for subsequent knee and hip osteoarthritis", Annals of Internal Medicine, vol. 133, pp. 321-328, 2000.
Gigout, A., "Chondrocyte Aggregation in Suspension Culture Is GFOGER-GPP- and β1 Integrin-dependent", Journal of Biological Chemistry, vol. 283, No. 46, pp. 31522-31530, 2008.
Goodrich L.R et al., "Medical treatment of osteoarthritis in the horse—a review" The Veterinary Journal, vol. 171, No. 1, pp. 51-69, 2006.
Gouttenoire, J. et al., "BMP-2 and TGF-β1 differentially control expression of type II procollagen and a10 and a11 integrins in mouse chondrocytes", European Journal of Cell Biology, 89, No. 4, pp. 307-314, 2010.
Hennig, T. et al., "Reduced chondrogenic potential of adipose tissue derived stromal cells correlates with an altered TGFβ receptor and BMP profile and is overcome by BMP-6", Journal of Cellular Physiology, vol. 211, No. 3, pp. 682-691, 2007.
Houard, X. et al., "Homeostatic Mechanisms in Articular Cartilage and Role of Inflammation in Osteoarthritis", Current Rheumatology Reports, 15(11):375, 2013.
Ilas, D. C. et al.,"Targeting subchondral bone mesenchymal stem cell activities for intrinsic joint repair in osteoarthritis", Future Science OA, vol. 3, No. 4, 2017.
Kawcak, C. E. et al., "The role of subchondral bone in joint disease: a review", Equine Veterinary Journal, vol. 33, No. 2, pp. 120-126, 2001.
Kidd, J. A. et al., "Osteoarthritis in the horse", Equine Veterinary Education, vol. 13, No. 3, pp. 160-168, 2001.
Kisiday, J. D et al., "Evaluation of adult equine bone marrow- and adipose-derived progenitor cell chondrogenesis in hydrogel cultures", Journal of Orthopaedic Research, vol. 26, pp. 322-331, 2008.
Li, G. et al. "Subchondral bone in osteoarthritis: insight into risk factors and microstructural changes", Arthritis Research & Therapy, vol. 15:223, 2013.
Lundgren-Åkerlund, E. et al., "Integrin a10β1: A Collagen Receptor Critical In Skeletal Development", Advances in Experimental Medicine and Biology, vol. 819, pp. 61-71, 2014.
McIlwraith C.W. et al., "Equine Models of Articular Cartilage Repair", Cartilage, vol. 2, No. 4, pp. 317-326, 2011.
Mundra, V. et al., "Mesenchymal stem cell-based therapy", Molecular Pharmaceutics, vol. 10, No. 1, pp. 77-89, 2013.
Nukavarapu, S. P. et al., "Osteochondral tissue engineering: Current strategies and challenges", Biotechnology Advances, vol. 31, pp. 706-721, 2013.
Raynaud, C.M. et al., "The Necessity of a Systematic Approach for the Use of MSCs in the Ciinicai Setting", Stem Cells International, pp. 1-10, 2013.
Samsonraj, R. M. et a;., "Establishing Criteria for Human Mesenchymal Stem Cell Potency", Stem Cells, vol. 33, pp. 1878-1891, 2015.
Schmutzer, M. et al., "Cell compaction influences the regenerative potential of passaged bovine articular chondrocytes in an ex vivo cartilage defect model", Journal of Bioscience and Bioengineering, vol. 123, No. 4, pp. 512-522, 2017.
Schnabel, Lauren V. et al., "Equine bone marrow-derived mesenchymal stromal cells are heterogeneous in MHC class II expression and capable of inciting an immune response in vitro", Stem Cell Research & Therapy, vol. 5, No. 13, 2014.
Schrobback, K. et al., "Stage-specific embryonic antigen-4 is not a marker for chondrogenic and osteogenic potential in cultured chondrocytes and mesenchymal progenitor cells", Tissue Engineering Part A, vol. 19, No. 11 & 12, pp. 1316-1326, 2013.
Spees, J. L. et al., "Mechanisms of mesenchymal stem/stromal cell function", Stem Ceil Research & Therapy, vol. 7:125, 2016.
Su, X. et al., "CD146 as a new marker for an increased chondroprogenitor cell sub-population in the later stages of osteoarthritis", Journal of Orthopaedic Research, vol. 33, No. 1, pp. 84-91, 2015.
Tailone, T. et al., "Adult human adipose tissue contains several types of muitipotent cells", Journal of Cardiovascular Translational Research, vol. 4, pp. 200-210, 2011.
Varas, L. et al., "Alpha10 integrin expression is upregulated on fibroblast growth factor-2-treated mesenchymal stem cells with improved chondrogenic differentiation potential", Stem Cells and Development, vol. 16, No. 6, pp. 965-978, Dec. 1, 2007.
Vidal, M.A et al., "Comparison of Chondrogenic Potential in Equine Mesenchymal Stromal Cells Derived from Adipose Tissue and Bone Marrow", Veterinary Surgery, vol. 37, No. 8, pp. 713-724, 2008.

* cited by examiner

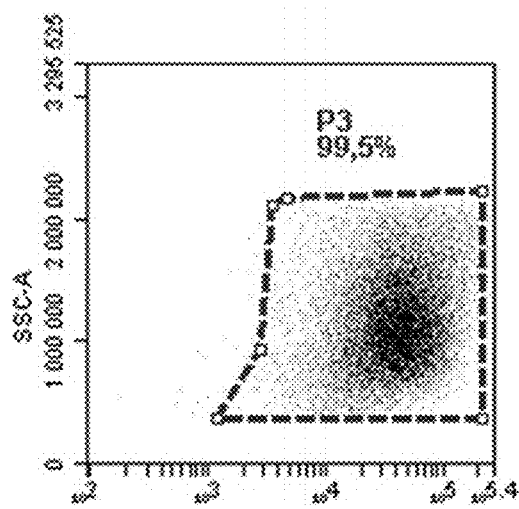 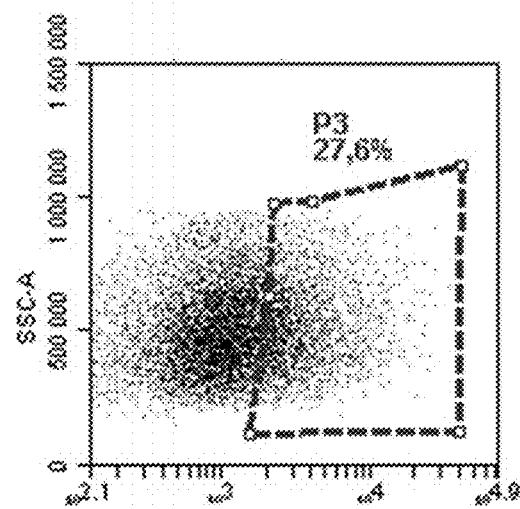
Fig. 2A                    Fig. 2B

PREVENTION AND TREATMENT OF BONE AND CARTILAGE DAMAGE OR DISEASE

CROSS REFERENCE TO RELATED APPLICATIONS

This application is a United States non-provisional continuation application filed under 35 U.S.C. § 111(a) of PCT Application No. PCT/EP2018/052104, filed on Jan. 29, 2018, which claims priority to U.S. Application No. 62/451,372, filed on Jan. 27, 2017, both of which are incorporated by reference in their entirety.

TECHNICAL FIELD

The present invention relates to compositions and methods for the prevention and/or treatment of conditions involving disease or damage in mammalian cartilage and bone, using mesenchymal stem cells isolated with anti-integrin α10 antibodies.

BACKGROUND

Articular cartilage is highly prone to injury and pathological degeneration. Once damaged, articular cartilage generally does not heal, or heals only partially under certain biological conditions. Damage leads to further degradation of the cartilage, and cartilage breakdown products initiate inflammation, resulting in further degradation of cartilage that in turn drives the inflammation, thus creating a vicious cycle[1]. There is a well-known link between early cartilage traumas, from sports injuries, for example, and later development of osteoarthritis (OA)[2].

Cell therapy is a promising method for tissue regeneration. A series of studies in animals and humans have shown safety and efficacy for the treatment of various diseases, including cartilage damage using multipotent mesenchymal stromal cells (MSCs)[6,7]. Therapeutic effects of MSCs are believed to be multifactorial. MSCs can directly differentiate into the specific cell type of the tissue to be regenerated, but also modify the microenvironment by producing extracellular matrix, cytokines and growth factors, recruit and stimulate endogenous stem cells, and have immunosuppressive effects[8]. Transplantation of MSCs for cartilage repair and regeneration is therefore a promising strategy given the potential of these cells to differentiate into chondrocytes[6]. Typically, stem cell preparations are complex mixtures of cell types or cells with varying capacities of differentiation. Because of their plasticity and large differentiation potential it is important that preclinical and clinical studies are conducted with well-defined cells.

Characterization of MSCs by quality controlled biomarkers is crucial for good efficacy but also for safe use of the cells as therapeutic agents. The international society for cellular therapy proposed the cell phenotypes plastic adherence, trilineage differentiation potential, as well as expression or absence of the surface markers CD73, CD90, CD105 respective CD45, CD34, CD14 or CD11b, CD79α or CD19, HLA-DR to be minimal criteria for human cells to be defined as MSCs[9].

In veterinary patients, three approaches based on MSCs are currently used for the treatment of tendon, ligament, or cartilage/joint injuries in horses or dogs[10]. The three cell types used are: a culture expanded cell population derived from bone marrow (BM) aspirate (most of the clinical studies have used this cell population), a concentrated mixed cell population derived from BM aspirate, and a mixed nucleated cell population derived from adipose tissue (AT). All three types of cells can be of autologous (own) or allogeneic (donor) origin. None of them have been very well defined.

To improve cartilage repair with MSCs, two variables are believed to be important for satisfactory results; the quality and number of MSCs to be injected and the administration method. It is now evident that cells selected by the international society for cellular therapy criteria, still are a heterogeneous population. A solution to the MSC quality problem could be to use a defined population of MSCs with expression of specific candidate potency markers[11].

Integrin alpha10 beta1 (α10β1) was originally identified as a collagen type II binding receptor on chondrocytes and has been shown to have a critical role in skeletal development[12]. It is abundantly expressed on chondrocytes and is present in a sub-population of human MSCs. Antibodies targeting integrin α10β1 can be used to identify, differentiate, and isolate MSCs from a mixed cell population (see WO03/106492). Extended culturing of chondrocytes or transforming growth factor (TGF) μ1 treatment leads to dedifferentiation accompanied by a decrease in the chondrocyte-specific integrin α10 level. In contrast, bone morphogenetic protein (BMP)-2 administration to the culture medium stabilizes the chondrogenic phenotype and induces high levels of integrin α10 expression[13]. In suspension culture, the formation of chondrocyte aggregates with distinct pericellular matrix requires α10β1 integrin-collagen type II interaction[14]. Moreover, it has been demonstrated that integrin α10β1 expression correlates with improved chondrogenic differentiation potential of human BM derived MSCs[15].

It is known that joint injury substantially increases the risk of osteoarthritis (OA), a phenomenon called post-traumatic osteoarthritis (PTOA). However, no preventative or disease modifying treatments are available for treatment of OA or PTOA, and current treatments alleviate symptoms without preventing the onset of disease and/or disease progression or worsening. Thus, there is a substantial need for means to prevent development of OA following injury or trauma.

SUMMARY

The present inventors have for the first time demonstrated in vivo that integrin α10 enriched populations of MSCs administered to mammals afflicted with bone or cartilage injuries, can be used to prevent and treat conditions associated therewith, or resulting therefrom.

Hence, in one aspect, the present disclosure is directed to an enriched integrin $\alpha 10^{high}$ population of MSCs for use in a method of prevention or treatment of subchondral bone sclerosis traumatic joint injuries, and/or degenerative disc disease, wherein at least 60% of the cells of the population of MSCs express integrin α10 subunit, and wherein said MSC is selected from the group consisting of a mesenchymal stem cell, a mesenchymal progenitor cell, and a mesenchymal stromal cell.

A further aspect of the present disclosure is directed to an enriched integrin $\alpha 10^{high}$ population of MSCs for promoting or inducing fracture healing, wherein at least 60% of the cells of the population of MSCs express integrin α10 subunit, and wherein said MSC is selected from the group consisting of a mesenchymal stem cell, a mesenchymal progenitor cell, and a mesenchymal stromal cell.

One aspect of the present disclosure is directed to a use of an enriched integrin $\alpha 10^{high}$ population of MSCs wherein at least 60% of the cells of the population of MSCs express integrin α10 subunit, and wherein said MSC is selected from the group consisting of a mesenchymal stem cell, a mesenchymal progenitor cell, and a mesenchymal stromal cell, for the preparation of a medicament for the prevention or treatment of subchondral bone sclerosis traumatic joint injuries, and/or degenerative disc disease.

A further aspect of the present disclosure is directed to a method of treating and/or preventing subchondral bone sclerosis traumatic joint injuries, and/or degenerative disc disease in a subject comprising administering an enriched integrin α10high population of MSC to a subject at risk for, or having, subchondral bone sclerosis, wherein at least 60% of the cells of the population of MSCs express integrin α10 subunit, and wherein said MSC is selected from the group consisting of a mesenchymal stem cell, a mesenchymal progenitor cell, and a mesenchymal stromal cell, thereby treating and/or preventing subchondral bone sclerosis and/or osteochondral damage.

One aspect of the present disclosure is directed to a method of manufacturing an enriched integrin $\alpha 10^{high}$ population of MSCs as described herein, the method comprising,
a. isolating a population of stem cells from adipose tissue, bone marrow, synovial membrane, cord blood, Wharton's jelly, or amniotic fluid;
b. culturing the isolated cells in a plastic culture vessel;
c. discarding non-adhered cells;
d. inducing integrin α10 expression by adding culture media, wherein the culture media is a serum-free media or a media comprising mammalian serum, and wherein the culture media comprises platelet lysate and/or platelet lysate components, and/or growth factors;
e. selecting the cells that express integrin α10, and
f. expanding the selected cells, thereby producing an enriched integrin $\alpha 10^{high}$ population of MSCs.

DESCRIPTION OF DRAWINGS

FIG. 2A and FIG. 2B show typical expression profiles of integrin α10β1 on cultured equine MSCs derived from BM (A) and AT (B). Integrin α10 labeling intensity was plotted against sidescatter. Both types of MSCs expressed integrin α10β1, but a larger proportion of BM derived MSCs were positive for integrin α10 expression.

DETAILED DESCRIPTION

Definitions

Figures 1A, 1B, 1C, 1D, 1E, 1F:
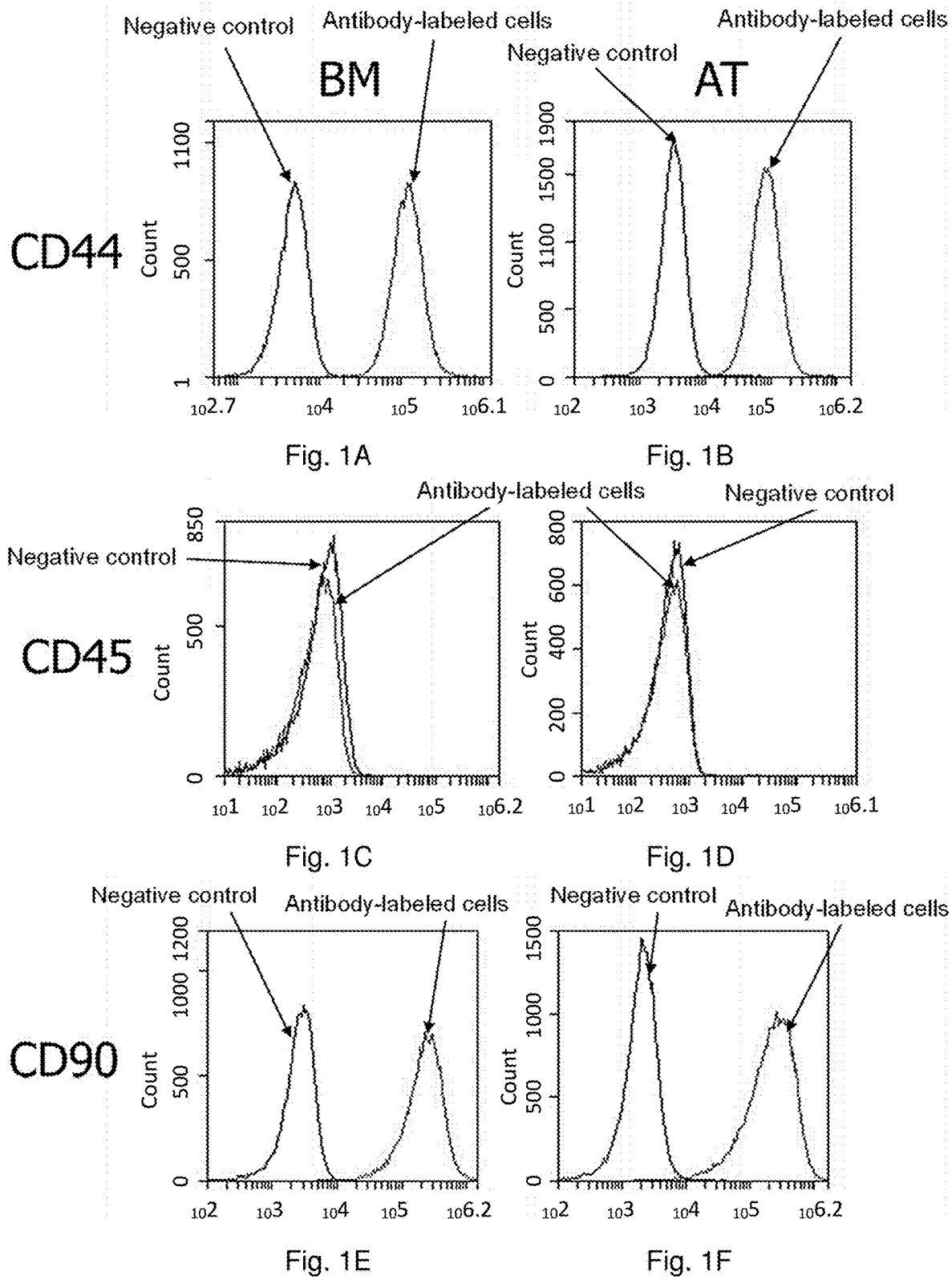
FIG. 1A, FIG. 1B, FIG. 1C, FIG. 1D, FIG. 1E, FIG. 1F, FIG. 1G, FIG. 1H, FIG. 1I, and FIG. 1J provide typical FACS profiles of bone marrow (BM) and adipose tissue (AT) derived mesenchymal stromal cells (MSCs). Cells were marked with antibodies recognizing the cell surface markers CD44, CD45, CD90, CD105, and MHC class II. The left panel shows BM derived MSCs, and the right panel shows AT derived MSCs. Antibody-labeled cells and negative control cells (not labeled with antibody) are shown.

"Anti-integrin α10 antibody" or "anti-integrin α10 subunit antibody" is used herein interchangeably to refer to an antibody capable of recognizing and binding to at least the integrin α10 subunit of the heterodimeric protein integrin α10β1. These antibodies may be antibodies that recognize an epitope of the heterodimeric protein integrin α10β1, wherein the epitope comprises amino acid residues of both the integrin α10 and the integrin β1 subunit.

The term "break" as used herein in relation to a bone injury or damage refers to a bone fracture, which is a medical condition in which there is a damage in the continuity of the bone. A break may be the result of high force impact or stress, but also of a minimal trauma injury as a result of certain medical conditions that weaken the bones, such as osteoporosis, bone cancer, or osteogenesis imperfecta, where the break or fracture can also be called pathologic fracture.

The term "bruise" as used herein in relation to a bone injury or damage refers to a traumatic injury to a fibrous tissue of a bone that is less severe than a bone fracture. A bone bruise may be cause by a traumatic injury to a bone or joint as well as by arthritis.

The term "identifying" as used herein refers to the action of recognizing a cell as being a certain type of cell, e.g. a MSC or a chondrocyte. An alternative term to identifying is "detecting", which is used herein with the same meaning.

"Integrin α10" or "integrin alpha-10" as used herein refers to the α10 subunit of the heterodimeric protein integrin α10β1. This denotation does not exclude the presence of the integrin β1 subunit bound to the integrin α10 subunit thus forming the quaternary structure of integrin α10β1 heterodimer. The human integrin α10 chain sequence is known and publicly available at GenBank®/EBI Data Bank accession number AF074015 and has been described in Camper et al J. Bio. Chem. 273:20383-20389 (1998).

The term "malalignment of a bone" as used herein refers to a displacement of a bone out of line in relation to joints.

The terms "isolating", "sorting" and "selecting" as used herein refer to the action of identifying a cell as being a certain type of cell and separating it from cells that do not belong to the same cell type or to another differentiation state. Usually, isolation refers to a first step of separation, whereas "selection" is more specific and for example performed with the help of an antibody.

"Mesenchymal stem cells" or "MSCs" as used herein refers to multipotent stromal cells as defined by The Mesenchymal and Tissue Stem Cell Committee of the International Society for Cellular Therapy (see Dominici M et al., Cytotherapy. 8(4):315-7 (2006)). MSCs must be plastic-adherent when maintained in standard culture conditions, and must express CD105, CD73 and CD90, and lack expression of CD45, CD34, CD14 or CD11b, CD79alpha or CD19 and HLA-DR surface molecules. MSCs must have the capacity to differentiate to osteoblasts, adipocytes or chondroblasts in vitro.

"Osteoarthritis" or "OA" as used herein refers to a joint disease characterized by breakdown of joint cartilage. OA may also be referred to as wear-and-tear arthritis, degenerative joint disease and degenerative arthritis. Symptoms of OA include joint swelling, pain, and decreased range of motion. Joints commonly affected by OA include the hand, large toe, wrist, neck, back, knee, and hip. In OA, cartilage may become stiff and lose its elasticity, or cartilage may wear away in some areas. In advanced cases of OA, the bones of a joint may rub against each other as joint surface cartilage is lost.

"Post-injury arthritis," "post-traumatic arthritis," or "PTOA" as used herein refers to OA caused by a previous injury, damage, or trauma. This condition may occur in any joint. Injury may damage the cartilage and/or bone of a joint, and this can cause cartilage to wear out more quickly. Conditions like continued injury or excess body weight may cause or accelerate the development of PTOA.

The term "sports injury" as defined herein refers to an injury that occur while exercising. Sports injuries can be both of traumatic nature and also due to overuse and repetitive stress.

The term "sprain" as used herein in relation to a bone injury or damage refers to a stretch and/or tear of a ligament. A sprain is usually caused by an injury that stresses a joint and overstretches or even ruptures supporting ligaments, for example a twist.

The term "tear" as used herein in relation to a bone injury or damage refers to rupturing of one or more of the fibrocartilage strips in a joint. Tear can be the result of a traumatic injury, such as a twist, but also of mild and prolonged stresses, in which case it can also be called degenerative tear. Tear are also referred to as ligaments ruptures.

"Treating," or "Treatment," as used herein, includes any administration or application of a therapeutic for the disclosed diseases, disorders and conditions in subject, and includes inhibiting the progression of the disease, slowing the disease or its progression, arresting its development, partially or fully relieving the disease, or partially or fully relieving one or more symptoms of a disease.

"Preventing" or "Prevention" as used herein, includes delaying or stopping the onset of disease, disorder, or condition.

Compositions

The invention comprises mesenchymal stem cell (MSCs) isolated from mixed cell populations with anti-integrin α10 antibodies. Therapeutically effective amounts of isolated MSCs may be administered to treat diseases/disorders like osteoarthritis, cartilage damage including fissuring, and subchondral bone sclerosis.

The invention comprises an enriched integrin α10$^{high}$ population of MSCs wherein the cells are induced to express integrin α10 subunit and wherein the enriched integrin α10$^{high}$ population of MSCs is a population wherein the percentage of MSCs expressing an integrin α10 subunit is at least 60% of the cells of the population.

In some embodiments at least 65%, such as at least 70%, such as at least 75%, such as at least 80%, such as at least 85%, such as at least 90%, such as at least 95%, such as at least 98%, such as at least 99%, such as at least 100% of the total cells comprised in the enriched integrin α10$^{high}$ population of MSCs express integrin α10 subunit.

In some embodiments the cells in the population of MSCs are induced to express integrin α10 subunit.

In some embodiments the integrin α10 is expressed as a heterodimer in combination with an integrin β1 subunit.

In some embodiments, the population of MSCs is derived from adipose tissue, bone marrow, synovial membrane, peripheral blood, cord blood, umbilical cord blood, Wharton's jelly, or amniotic fluid. Preferably, in some embodiments, the population of MSCs is derived from adipose tissue. Preferably, in some embodiments, the population of MSCs is derived from bone marrow.

In some instances, the enriched integrin α10$^{high}$ population of MSCs is cultured in a plastic culture dish and induced to express integrin α10.

In some embodiments, the cells are cultured in a culture media comprising mammalian serum and FGF-2. In some embodiments, the cells are cultured in a culture media comprising platelet lysate and/or platelet lysate components. The term "platelet lysate components" refers to a composition comprising only some of the elements that are usually found in platelet lysate. For example, specific growth factor may be selected or de-selected. In some embodiments, the cells are cultured in a culture media comprising FGF-2 and platelet lysate and/or platelet lysate components. In some embodiments, the cells are cultured in a culture media comprising mammalian serum and platelet lysate and/or platelet lysate components. In some embodiments, the cells are cultured in a culture media comprising TGFβ. In some embodiments the cells are cultured in a serum-free culture media. In some embodiments the cells are cultured in a serum-free culture media comprising platelet lysate and/or platelet lysate components. In some embodiments the cells are cultured in a serum-free culture media comprising growth factors, for example FGF-2 and/or TGFβ. In some embodiments the cells are cultured in a culture media comprising mammalian serum, and the mammalian serum is fetal bovine serum. The examples of culture media herein above are all suitable for inducing the cells to express integrin α10. However, other culture media suitable for inducing the cells to express integrin α10 exist and are known to the person skilled in the art.

In some embodiments, the enriched integrin α10$^{high}$ population of MSCs is an in vitro cell culture.

In some embodiments, the cells are cultured in a culture media that further comprises ascorbic acid.

In some embodiments, the cells are stored in a culture media that further comprises dimethyl sulfoxide (DMSO). DMSO may be present in the culture media for storage purposes in volume comprised between 0 and 12% of the total culture volume, preferably at least 1%, such as at least 2%, for example at least 3%, preferably at least 4%, such as at least 5%, for example at least 6%, preferably at least 7%, such as at least 8%, for example at least 9%, preferably at least 10% of the total culture volume. DMSO is beneficial for storage of cells because it facilitates freezing and thawing of the cell culture so that the cells can be directly administered to the subject in need after thawing. DMSO may also be eliminated after thawing by washing the cells.

In some embodiments DMSO facilitates the preventive or treating action of the MSCs by reducing soft tissue swelling, inflammation, and edema secondary to acute trauma, increased blood flow and promote vascular dilation In some embodiments, the invention comprises a MSCs that expresses integrin α10, CD44, CD90, and CD105, and lacks MHCII and CD45.

In some embodiments, the population of MSCs is derived from fetal, neonatal, juvenile or adult MSCs and/or progenitor cells.

In some embodiments, the population of MSCs are not derived from embryonic cells or from an embryo.

In some embodiments, the invention comprises an in vitro cell culture comprising undifferentiated MSCs expressing an integrin α10 subunit.

In some embodiments, the cells are derived from adipose or bone marrow tissue. In some embodiments, the cells in the culture have the capacity to differentiate into chondrocytes. In some embodiments, the cell culture comprises at least 1%, at least 2%, at least 3%, at least 4%, at least 5%, at least 6%, at least 7%, at least 8%, at least 9%, at least 10%, at least 20%, at least 30%, at least 40%, at least 50%, at least 60%, at least 70%, at least 80%, or at least 90% chondrocytes after differentiation. In some embodiments, the cells divide in a culture medium containing serum and at least one proliferation-inducing growth factor. In some embodiments, cells in the culture differentiate into chondrocytes upon withdrawal of both serum and the proliferation inducing growth factor. In some embodiments, the at least one proliferation-inducing growth factor is selected from a group consisting of fibroblast growth factor (FGF)-2 or platelet lysate or combinations thereof.

In some embodiments, the invention comprises a population of MSCs in a culture dish, wherein the cells had or previously had contact with media containing an ingredient that induces expression of integrin α10, and wherein the percentage of integrin α10 positive cells comprises at least 10%, at least 20%, at least 30%, at least 40%, at least 50%, at least 60%, at least 70%, at least 80%, at least 90%, or at least 95% of the total cells. Preferably, the percentage of integrin α10 positive cells comprised in the enriched integrin α10$^{high}$ population comprises at least 60%, at least 65%, at least 70%, at least 75%, at least 80%, at least 85%, at least 90%, at least 95%, at least 98% or 100% of the total cells.

In some embodiments, the invention comprises MSCs in a suspension culture, wherein the cells express an integrin α10 subunit or an integrin α10 polypeptide.

In some embodiments, the cells in suspension are substantially formed into cell aggregates. For example, the aggregates may be in the form of pellets or spheroids. In some embodiments, the cell aggregates are maintained in a culture medium containing a proliferation-inducing growth factor.

In some embodiments, the enriched integrin α10$^{high}$ population of MSCs further expresses at least one of CD44, CD90 or CD105. In some embodiments, the enriched integrin α10$^{high}$ population of MSCs further expresses both of CD44, CD90 and/or CD105. In some embodiments, the enriched integrin α10$^{high}$ population of MSCs does not express MHCII or CD45.

In some embodiments, the cells in the culture are human, murine, canine or equine. In some embodiments, the cells in the culture are human. In some embodiments, the cells in the culture are equine. In some embodiments, the cells in the culture are canine.

In some embodiments, the cells in the enriched integrin α10$^{high}$ population are selected from the group consisting of a mesenchymal stem cell, a mesenchymal progenitor cell, and a mesenchymal stromal cell.

In some embodiments, the cells in the enriched integrin α10$^{high}$ population are derived from human fetal, neonatal, juvenile or human adult MSCs. In some embodiments, the cells in the culture are not derived from human embryonic cells or from a human embryo.

In some embodiments, MSCs are cultured to expand in numbers and induce expression of integrin α10.

In some embodiments, MSCs adhere to plastic culture dish. In some embodiments, non-adherent cells are discarded.

In some embodiments, integrin α10 expression is induced by addition of defined media. In some embodiments, this defined media is DMEM supplemented with fetal bovine serum and FGF-2; DMEM supplemented with platelet lysate; or commercially-available chemically defined media with factors that perform the same function as FGF-2 or platelet lysate. In some embodiments the enriched integrin α10$^{high}$ population of MSCs is cultured in a culture media that comprises DMEM/F12, PRIME-XV® MSC Expansion SFM or STEMMACS.

In some embodiments, cells that express integrin α10 are isolated with an anti-integrin α10 antibody. For example, the anti-integrin α10 antibody may be a monoclonal antibody. In some embodiments, the antibody is produced by immunizing mice with a human integrin α10 polypeptide. In some embodiments, cells that do not express integrin α10 are discarded.

In some embodiments the in vitro cell culture enriched for integrin α10 expressing MSCs or the MSCs expressing integrin α10 isolated from the in vitro cell culture are frozen and stored in closed plastic vials made of, for example, cyclic olefin copolymer (COC) or any equivalent material. Prior to administration to a subject in need thereof, the frozen cells are thawed and can be administered without further treatment, or after washing.

In some embodiments, the population of MSCs is formulated into a cell aggregate prior to administration, usually even prior to freezing. The cell aggregate may be in the form of a spheroid or of a pellet. It is advantageous to administer the cells in aggregate form because they will have a better homing capacity and they better mimic cartilage.

In some embodiments the in vitro cell culture enriched for integrin α10 expressing MSCs or the MSCs expressing integrin α10 isolated from the in vitro cell culture are used as a somatic cell therapy medicinal product or as a tissue engineered product.

Methods of Treatment

The present disclosure relates to methods for preventing and/or treating subchondral bone sclerosis and/or osteochondral damage comprising administering to the subject in need an enriched integrin α10$^{high}$ population of MSCs.

The present disclosure relates to methods for preventing and/or treating degenerative joint disease (DJD), traumatic joint injuries, and/or degenerative disc disease comprising administering to the subject in need an enriched integrin α10$^{high}$ population of MSCs.

In some embodiments the DJD is selected from a group consisting of subchondral bone sclerosis, subchondral bone disease, cartilage degeneration, post-traumatic osteoarthritis, inflammatory arthritis, and congenital malformation and/or deformation of the musculoskeletal system.

In some embodiments the traumatic joint injury comprises sport injuries.

In some embodiments the traumatic joint injury is selected from a group consisting of osteochondral damage, tendon damage, ligament damage, and muscle damage.

In some embodiments, the osteochondral damage comprises articular cartilage damage and/or bone damage.

In some embodiments, the methods of the present disclosure may be used for treatment or prevention of arthritis.

The enriched integrin α10$^{high}$ population of MSCs used in the methods disclosed herein is described in detail in the section above "Compositions".

One of the advantages of the methods disclosed herein is that the enriched integrin α10$^{high}$ population of MSCs, thanks to the integrin α10 expression, can effectively as high adherence and can easily attach to the damaged bone or cartilage.

In some embodiments, the methods of preventing subchondral bone sclerosis and/or osteochondral damage as disclosed herein comprise administering the MSCs cells induced to express integrin α10 shortly after an injury to a joint has occurred, for example the same day, within one week, within two weeks, within three weeks, within one month, within two months, within 3 months, or within less than one year from the day of the injury. The administered MSCs can for example repair the initial damage in bone and cartilage thus preventing or minimizing the development of subchondral bone sclerosis and progressive cartilage degradation, which might otherwise develop into osteoarthritis. In fact, as a progressive degenerative joint disorder, osteoarthritis is characterized by cartilage damage, changes in the subchondral bone, osteophyte formation, muscle weakness, and inflammation of the synovium tissue and tendon. Although osteoarthritis has long been viewed as a primary disorder of articular cartilage, subchondral bone is attracting increasing attention. It is commonly reported to play a vital role in the pathogenesis of osteoarthritis. Subchondral bone sclerosis, together with progressive cartilage degradation, is widely considered as a hallmark of osteoarthritis (Guangyi Li, Jimin Yin, Junjie Gao, Tak S Cheng, Nathan J Pavlos, Changqing Zhang, and Ming H Zheng; Subchondral bone in osteoarthritis: insight into risk factors and microstructural changes; Arthritis Res Ther. 2013; 15(6): 223; and Castaneda S, Roman-Blas J A, Largo R, Herrero-Beaumont G; Subchondral bone as a key target for osteoarthritis treatment; Biochem Pharmacol. 2012 Feb. 1; 83(3):315-23). Moreover osteochondral lesions or osteochondritis dessicans can occur in any joint, but are most common in the knee and ankle. Such lesions are a tear or fracture in the cartilage covering one of the bones in a joint. The cartilage can be torn, crushed or damaged and, in rare cases, a cyst can form in the cartilage. The present disclosure provides methods for treating subchondral bone sclerosis, hence the same methods may be used for successfully preventing osteoarthritis.

In some embodiments, the methods of treating subchondral bone sclerosis and/or osteochondral damage as disclosed herein comprise administering the MSCs cells induced to express integrin α10 to a subject diagnosed with subchondral bone sclerosis and/or osteochondral damage. The administered MSCs cells induced to express integrin α10 can decrease a thickening in the subchondral layer of a joint and/or decrease an increase in bone density in a joint, thereby treating subchondral bone sclerosis and/or osteochondral damage.

An "osteochondral damage or injury" as used herein is an injury to the smooth surface on the end of bones, called articular cartilage (chondro), and also to the bone (osteo) underneath it. The degree of injury ranges from a small crack to a piece of the bone breaking off inside the joint. These fragments can be of many sizes and depths and can stay attached (stable) to the area that was injured or become loose (unstable) inside the joint. This injury is more common in adolescents and young adults and typically occurs at the knee, ankle or elbow. In particular, recognised sites of osteochondral defects are: femoral condyle (most common); humeral head; talus; and capitellum of the humerus. It is a term that encompasses osteochondritis dissecans and is used synonymously with osteochondral damage or injury.

In some embodiments, the method comprises treating osteoarthritis in a subject comprising administering an enriched integrin $\alpha 10^{high}$ population of MSCs or an MSC that has been isolated from a population of MSCs using an anti-integrin $\alpha 10$ antibody to a subject who has, or is at risk for, osteoarthritis, thereby treating osteoarthritis.

In some embodiments, the method comprises delaying or preventing the progression of osteoarthritis in a subject comprising administering a enriched integrin $\alpha 10^{high}$ population of MSCs that has been isolated from a population of MSCs using an anti-integrin $\alpha 10$ antibody to a subject who has osteoarthritis, wherein the progression of osteoarthritis is delayed as compared to a control who is not administered the MSC.

In some embodiments, the method comprises treating subchondral bone sclerosis comprising administering an enriched integrin $\alpha 10^{high}$ population of MSCs or an isolated MSC that has been isolated from a population of MSCs using an anti-integrin $\alpha 10$ antibody, thereby treating subchondral bone sclerosis.

In some embodiments, treating subchondral bone sclerosis comprises preventing or reversing increase in bone formation around a joint. In some embodiments, treating subchondral bone sclerosis comprises preventing or decreasing a thickening in the subchondral layer of a joint or preventing or decreasing an increase in bone density in a joint.

In some embodiments, the method comprises treating a degenerative bone and joint disease comprising administering an enriched integrin $\alpha 10^{high}$ population of MSCs or an isolated MSC that has been isolated from a population of MSCs using an anti-integrin $\alpha 10$ antibody, thereby treating a degenerative bone and joint disease.

In some embodiments, the method comprises preventing a degenerative bone and joint disease comprising administering an enriched integrin $\alpha 10^{high}$ population of MSCs or an isolated MSC that has been isolated from a population of MSCs using an anti-integrin $\alpha 10$ antibody, thereby preventing a degenerative bone and joint disease.

In some embodiments, the subchondral bone sclerosis or osteochondral damage is a degenerative joint disease or congenital malformation and/or deformation of the musculoskeletal system.

In some embodiments, the subchondral bone sclerosis or osteochondral damage is a degenerative joint disease selected from a group consisting of osteoarthritis, inflammatory arthritis, degenerative disk disease, sport injuries, traumatic joint injuries.

In some embodiments, the method comprises treating a sport injury comprising administering an enriched integrin $\alpha 10^{high}$ population of MSCs or an isolated MSC that has been isolated from a population of MSCs using an anti-integrin $\alpha 10$ antibody, thereby treating a sport injury.

In some embodiments, the method comprises treating a post-traumatic osteoarthritis (PTOA) comprising administering an enriched integrin $\alpha 10^{high}$ population of MSCs or an isolated MSC that has been isolated from a population of MSCs using an anti-integrin $\alpha 10$ antibody, thereby treating a PTOA.

In some embodiments, the administering of the MSC compositions described herein results in increased collagen production at the site of administration. In some embodiments, the administering of the composition results in increased type II collagen synthesis. In some embodiments, increased type II collagen synthesis is measured using a ProCollagen II C-Propeptide Assay that measures the released carboxy propeptide in the formation of collagen, and therefore reflects changes in the rate of collagen type II synthesis. CPII tended to be greater in synovial fluid from treated limbs compared to control limbs. In some embodiments, the administering of the composition results in increased proteoglycan production, and/or lubricin.

In some embodiments, a method of treating cartilage fissuring in a subject comprises administering an enriched integrin $\alpha 10^{high}$ population of MSCs or a MSC that has been isolated from a population of MSCs using an anti-integrin $\alpha 10$ antibody, thereby treating cartilage fissuring. In some embodiments, cartilage fissuring comprises cartilage fibrillation. In some embodiments, the cartilage fissure is in articular cartilage or cartilage at the end of bones. In some embodiments, the cartilage fissure occurs when there is cleavage within layers of cartilage causing a separation between the layers. The cartilage fissuring may be an osteochondral damage, cartilage damage or injury.

In some embodiments, treating cartilage fissuring comprises a reduction in structural damage in the area of injury. In some embodiments, treating cartilage fissuring comprises preventing cartilage damage.

In some embodiments, MSCs are administered in the form of cell aggregates. In some embodiments, MSCs are administered as a pellet. Means to administer MSCs as pellets are known by those skilled in the art (see Bartz et al J. Trans) Med. 14:317 (2016), hereby incorporated by reference). In some embodiments, MSCs may be administered after differentiation to chondrocytes as spheroids or as matrix-associated chondrocyte implants. These administration forms result in easier homing of the cells into the damaged site.

In some embodiments, enriched integrin $\alpha 10^{high}$ population of MSCs are administered as a cell suspension. Pharmaceutically effective amounts of MSCs are administered. MSCs may be administered together with a pharmaceutically acceptable excipient.

In some embodiments, the enriched integrin $\alpha 10^{high}$ population of MSCs are administered to a subject that has, or previously had, osteochondral damage, cartilage damage or an injury to a joint or bone. In some embodiments, the osteochondral damage, cartilage damage or injury is a break, sprain, bruise, or tear. For example, the damage may be cartilage fissure or ligament fibrillation. In some embodiments, the osteochondral damage, cartilage damage or injury is a cartilage microfracture. In some embodiments, the osteochondral damage, cartilage damage or injury is a chondral defect. In some embodiments, the osteochondral damage, cartilage damage or injury is the result of wearing a prosthesis. For example, the osteochondral damage, cartilage damage or injury in the joint is in a muscle, tendon, bone, ligament, cartilage, or meniscus.

In some embodiments, the enriched integrin $\alpha 10^{high}$ population of MSCs are administered to a subject having malalignment of a bone.

The enriched integrin $\alpha 10^{high}$ population of MSCs may be administered after an injury to prevent the onset of disease.

The enriched integrin α10$^{high}$ population of MSCs may be administered after an injury during a surgical repair of the injured joint and/or bone site. In some embodiment the enriched integrin α10$^{high}$ population of MSCs is administered at the same time as setting a bone after a break, for example when repairing a fractured bone.

In some embodiments the enriched integrin α10$^{high}$ population of MSCs has anti-inflammatory effect. Nevertheless, the enriched integrin α10$^{high}$ population of MSCs may be administered at the same time as, before, or after the administration of another therapy, such as, for example, an anti-inflammatory agent.

In some embodiment the enriched integrin α10$^{high}$ population of MSCs may be administered into a joint cavity. The enriched integrin α10$^{high}$ population of MSCs may be administered via injection.

In some embodiment the enriched integrin α10$^{high}$ population of MSCs is administered to a subject, wherein the subject is a human, horse, pony, ox, donkey, mule, camelid, cat, dog, pig, or cow. In preferred embodiments, the subject is human. In other preferred embodiment, the subject is horse. In further preferred embodiments, the subject is dog.

In some embodiments, the administered enriched integrin α10$^{high}$ population of MSCs are allogeneic or autologous. In some embodiment the enriched integrin α10$^{high}$ population of MSCs and the subject are from the same species or genus. In some embodiment the enriched integrin α10$^{high}$ population of MSCs and the subject are from a different species or genus.

In some embodiments the in vitro cell culture enriched for integrin α10 expressing MSCs or the MSCs expressing integrin α10 isolated from the in vitro cell culture are administered as a somatic cell therapy medicinal product or as a tissue engineered product.

Methods of Manufacturing

One aspect of the present disclosure relates to a method of manufacturing the enriched integrin α10$^{high}$ population of MSCs as disclosed herein, the method comprising,
 a. isolating a population of stem cells from adipose tissue, bone marrow, synovial membrane, cord blood, Wharton's jelly, or amniotic fluid;
 b. culturing the isolated cells in a plastic culture vessel;
 c. discarding non-adhered cells;
 d. inducing integrin α10 expression by adding culture media, wherein the culture media is a serum-free media or a media comprising mammalian serum, and wherein the culture media comprises platelet lysate and/or platelet lysate components, and/or growth factors;
 e. selecting the cells that express integrin α10, and
 f. expanding the selected cells, thereby producing an enriched integrin α10$^{high}$ population of MSCs.

In some embodiments, the cells during induction of integrin α10 expression are cultured in a culture media as described in the section above "Composition".

In some embodiments, the cells that express integrin α10 are selected in step e. using an anti-integrin α10 antibody, as described herein above.

In some embodiments, enriched integrin α10$^{high}$ population of MSCs obtained is as described in the section above "Composition".

In some embodiments, the cells are cultured in media that do not comprise mammalian serum. For example, in some embodiments the cells are cultured in media that comprises or consists of platelet lysate or platelet lysate components.

Items

1. An enriched integrin α10$^{high}$ population of mesenchymal stem cells (MSCs), wherein at least 60% of the cells of the population of MSCs express integrin α10 subunit.
2. The enriched integrin α10$^{high}$ population of MSCs according to item 1, wherein at least 65%, such as at least 70%, such as at least 75%, such as at least 80%, such as at least 85%, such as at least 90%, such as at least 95%, such as at least 96%, such as at least 97%, such as at least 98%, such as at least 99%, such as at least 100% of the total cells comprised in the population express integrin α10 subunit.
3. The enriched integrin α10$^{high}$ population of MSCs according to any one of the preceding items, wherein the cells are induced to express integrin α10 subunit.
4. The enriched integrin α10$^{high}$ population of MSCs according to any one of the preceding items, wherein the cells are cultured in a culture media comprising mammalian serum and FGF-2.
5. The enriched integrin α10$^{high}$ population of MSCs according to any one of the preceding items, wherein the cells are cultured in a culture media comprising platelet lysate and/or platelet lysate components.
6. The enriched integrin α10$^{high}$ population of MSCs according to any one of the preceding items, wherein the cells are cultured in a culture media comprising FGF-2 and platelet lysate and/or platelet lysate components.
7. The enriched integrin α10$^{high}$ population of MSCs according to any one of the preceding items, wherein the cells are cultured in a culture media comprising mammalian serum and platelet lysate and/or platelet lysate components.
8. The enriched integrin α10$^{high}$ population of MSCs according to any one of the preceding items, wherein the cells are cultured in a culture media comprising TGFβ.
9. The enriched integrin α10$^{high}$ population of MSCs according to any one of the preceding items, wherein the cells are cultured in a serum-free culture media comprising platelet lysate and/or platelet lysate components.
10. The enriched integrin α10$^{high}$ population of MSCs according to any one of the preceding items, wherein the cells are cultured in a serum-free culture media comprising growth factors.
11. The enriched integrin α10$^{high}$ population of MSCs according to any one of the preceding items, wherein the cells are cultured in a serum-free culture media comprising the growth factors FGF2 and/or TGFβ.
12. The enriched integrin α10$^{high}$ population of MSCs according to any one of the preceding items, wherein said population is an in vitro cell culture.
13. A MSC isolated from the population of any one of the preceding items with an anti-integrin α10 antibody.
14. An enriched integrin α10$^{high}$ population of MSCs for use in a method of prevention or treatment of degenerative joint disease (DJD), traumatic joint injuries, and/or degenerative disc disease,
    wherein at least 60% of the cells of the population of MSCs express integrin α10 subunit, and
    wherein said MSC is selected from the group consisting of a mesenchymal stem cell, a mesenchymal progenitor cell, and a mesenchymal stromal cell.
15. An enriched integrin α10$^{high}$ population of MSCs for use in a method of prevention or treatment of degenerative joint disease (DJD), traumatic joint injuries, degenerative disc disease, cartilage degeneration, subchondral bone sclerosis, post traumatic osteoarthritis, inflammatory arthritis, subchondral bone disease, sport injuries, osteochondral damage, articular cartilage damage, bone damage, tendon damage, ligament damage and/or muscle damage,
wherein at least 60% of the cells of the population of MSCs express integrin α10 subunit, and
wherein said MSC is selected from the group consisting of a mesenchymal stem cell, a mesenchymal progenitor cell, and a mesenchymal stromal cell.

16. The enriched integrin $\alpha 10^{high}$ population of MSCs for use according to item 14, wherein DJD is selected from a group consisting of subchondral bone sclerosis, subchondral bone disease, cartilage degeneration, post-traumatic osteoarthritis, inflammatory arthritis, and congenital malformation and/or deformation of the musculoskeletal system.

17. The enriched integrin $\alpha 10^{high}$ population of MSCs for use according to any one of items 14 and 16, wherein the traumatic joint injury comprises sport injuries.

18. The enriched integrin $\alpha 10^{high}$ population of MSCs for use according to any one of items 14 to 17, wherein the traumatic joint injury is selected from a group consisting of osteochondral damage, tendon damage, ligament damage, and muscle damage.

19. The enriched integrin $\alpha 10^{high}$ population of MSCs for use according to any one of items 14 and 18, wherein the osteochondral damage comprises articular cartilage damage and/or bone damage.

20. An enriched integrin $\alpha 10^{high}$ population of MSCs for promoting or inducing fracture healing, wherein at least 60% of the cells of the population of MSCs express integrin α10 subunit, wherein said MSC is selected from the group consisting of a mesenchymal stem cell, a mesenchymal progenitor cell, and a mesenchymal stromal cell.

21. The enriched integrin $\alpha 10^{high}$ population of MSCs for use according to any one of items 14 to 20, wherein at least 65%, such as at least 70%, such as at least 75%, such as at least 80%, such as at least 85%, such as at least 90%, such as at least 95%, such as at least 96%, such as at least 97%, such as at least 98%, such as at least 99%, such as at least 100% of the total cells comprised in the population express integrin α10 subunit.

22. The enriched integrin $\alpha 10^{high}$ population of MSCs for use according to any one of items 14 to 21, wherein the cells are induced to express integrin α10 subunit.

23. The enriched integrin $\alpha 10^{high}$ population of MSCs for use according to any one of items 14 to 22, wherein the cells are cultured in a culture media comprising mammalian serum and FGF-2.

24. The enriched integrin $\alpha 10^{high}$ population of MSCs for use according to any one of items 14 to 23, wherein the cells are cultured in a culture media comprising platelet lysate and/or platelet lysate components.

25. The enriched integrin $\alpha 10^{high}$ population of MSCs for use according to any one of items 14 to 24, wherein the cells are cultured in a serum-free culture media comprising platelet lysate and/or platelet lysate components.

26. The enriched integrin $\alpha 10^{high}$ population of MSCs for use according to any one of items 14 to 25, wherein the cells are cultured in a serum-free culture media comprising growth factors, wherein the growth factors are FGF2 and/or TGFβ.

27. The enriched integrin $\alpha 10^{high}$ population of MSCs for use according to any one of items 14 to 26, wherein the cells are cultured in a culture media comprising FGF-2 and platelet lysate and/or platelet lysate components.

28. The enriched integrin $\alpha 10^{high}$ population of MSCs for use according to any one of items 14 to 27, wherein the cells are cultured in a culture media comprising mammalian serum and platelet lysate and/or platelet lysate components.

29. The enriched integrin $\alpha 10^{high}$ population of MSCs for use according to any one of items 14 to 28, wherein the cells are cultured in a culture media comprising TGFβ.

30. The enriched integrin $\alpha 10^{high}$ population of MSCs for use according to any one of items 14 to 29, wherein said serum is fetal bovine serum.

31. The enriched integrin $\alpha 10^{high}$ population of MSCs for use according to any one of items 14 to 30, wherein said population is an in vitro cell culture.

32. The enriched integrin $\alpha 10^{high}$ population of MSCs for use according to any one of items 14 to 31, wherein said culture media further comprises ascorbic acid.

33. The enriched integrin $\alpha 10^{high}$ population of MSCs for use according to any one of items 14 to 32, wherein said MSC is selected from the group consisting of a mesenchymal stem cell, a mesenchymal progenitor cell, and a mesenchymal stromal cell.

34. The enriched integrin $\alpha 10^{high}$ population of MSCs for use according to any one of items 14 to 33, wherein the integrin α10 is expressed as a heterodimer in combination with an integrin β1 subunit.

35. The enriched integrin $\alpha 10^{high}$ population of MSCs for use according to any one of items 14 to 34, wherein the cells that express integrin α10 are isolated with an anti-integrin α10 antibody.

36. The enriched integrin $\alpha 10^{high}$ population of MSCs for use according to any one of items 14 to 35, wherein the anti-integrin α10 antibody is a monoclonal antibody.

37. The enriched integrin $\alpha 10^{high}$ population of MSCs for use according to any one of items 14 to 36, wherein the antibody is produced by immunizing mice with a human integrin α10 polypeptide.

38. The enriched integrin $\alpha 10^{high}$ population of MSCs for use according to any one of items 14 to 37, wherein the MSCs are further characterized by an absence of MHCII and CD45.

39. The enriched integrin $\alpha 10^{high}$ population of MSCs for use according to any one of items 14 to 38, wherein the MSCs are further characterized by the presence of CD44, CD90 and CD105.

40. The enriched integrin $\alpha 10^{high}$ population of MSCs for use according to anyone of items 14 to 39, wherein the cells are derived from adipose tissue, bone marrow, synovial membrane, peripheral blood, cord blood, umbilical cord blood, Wharton's jelly, or amniotic fluid.

41. The enriched integrin $\alpha 10^{high}$ population of MSCs for use according to any one of items 14 to 40, wherein the cells are derived from adipose tissue.

42. The enriched integrin $\alpha 10^{high}$ population of MSCs for use according to any one of items 14 to 41, wherein the cells are derived from bone marrow.

43. The enriched integrin $\alpha 10^{high}$ population of MSCs for use according to any one of items 14 to 42, wherein the population is for use in a method of prevention of subchondral bone disease and/or osteochondral damage.

44. The enriched integrin $\alpha 10^{high}$ population of MSCs for use according to any one of items 14 to 43, wherein the population is for use in a method of treatment of subchondral bone disease and/or osteochondral damage.

45. The enriched integrin $\alpha 10^{high}$ population of MSCs for use according to any one of items 14 to 44, wherein the subject has, or previously had, osteochondral damage, cartilage damage or an injury to a joint or bone.

46. The enriched integrin $\alpha10^{high}$ population of MSCs for use according to any one of items 14 to 45, wherein the osteochondral damage, cartilage damage or injury is a break, sprain, bruise, tear, fracture or rupture.

47. The enriched integrin $\alpha10^{high}$ population of MSCs for use according to any one of items 14 to 46, wherein the osteochondral damage, cartilage damage or injury is a cartilage fissure.

48. The enriched integrin $\alpha10^{high}$ population of MSCs for use according to any one of items 14 to 47, wherein the osteochondral damage, cartilage damage or injury is a cartilage microfracture.

49. The enriched integrin $\alpha10^{high}$ population of MSCs for use according to any one of items 14 to 48, wherein the osteochondral damage, cartilage damage or injury is a chondral defect.

50. The enriched integrin $\alpha10^{high}$ population of MSCs for use according to any one of items 14 to 49, wherein the osteochondral damage, cartilage damage or injury is a tendon rupture or a ligament rupture.

51. The enriched integrin $\alpha10^{high}$ population of MSCs for use according to any one of items 14 to 50, wherein the osteochondral damage, cartilage damage or injury is a bone fracture.

52. The enriched integrin $\alpha10^{high}$ population of MSCs for use according to any one of items 14 to 51, wherein the injury is a sports injury.

53. The enriched integrin $\alpha10^{high}$ population of MSCs for use according to any one of items 14 to 52, wherein the subject has malalignment of a bone.

54. The enriched integrin $\alpha10^{high}$ population of MSCs for use according to any one of items 14 to 53, wherein osteochondral damage, cartilage damage or injury is the result of wearing a prosthesis.

55. The enriched integrin $\alpha10^{high}$ population of MSCs for use according to any one of items 14 to 54, wherein the osteochondral damage, cartilage damage or injury in the joint is in a muscle, tendon, bone, ligament, cartilage, or meniscus.

56. The enriched integrin $\alpha10^{high}$ population of MSCs for use according to any one of items 14 to 55, wherein the method prevents post-traumatic osteoarthritis (PTOA) resulting from subchondral bone disease or osteochondral damage.

57. The enriched integrin $\alpha10^{high}$ population of MSCs for use according to any one of items 14 to 56, wherein the MSCs are allogeneic or autologous.

58. The enriched integrin $\alpha10^{high}$ population of MSCs for use according to any one of items 14 to 57, wherein the MSCs are administered into a joint cavity.

59. The enriched integrin $\alpha10^{high}$ population of MSCs for use according to any one of items 14 to 58, wherein the population of MSCs is administered via injection.

60. The enriched integrin $\alpha10^{high}$ population of MSCs for use according to any one of items 14 to 59, wherein the population of MSCs is administered in a cell suspension with a pharmaceutically acceptable excipient.

61. The enriched integrin $\alpha10^{high}$ population of MSCs for use according to any one of items 14 to 60 wherein the population of MSCs is formulated into a cell aggregate prior to administration.

62. The enriched integrin $\alpha10^{high}$ population of MSCs for use according to any one of items 14 to 61, wherein the population of MSCs is administered during a surgery to repair a damaged joint and/or bone.

63. The enriched integrin $\alpha10^{high}$ population of MSCs for use according to any one of items 14 to 62, wherein the population of MSCs is administered at the same time as setting a bone after a break.

64. The enriched integrin $\alpha10^{high}$ population of MSCs for use according to any one of items 14 to 63, wherein the subject is a human, horse, pony, ox, donkey, mule, camelid, cat, dog, pig, or cow.

65. The enriched integrin $\alpha10^{high}$ population of MSCs for use according to any one of items 14 to 64, wherein the subject is human.

66. The enriched integrin $\alpha10^{high}$ population of MSCs for use according to any one of items 14 to 65, wherein the subject is horse.

67. The enriched integrin $\alpha10^{high}$ population of MSCs for use according to any one of items 14 to 66, wherein the subject is dog.

68. The enriched integrin $\alpha10^{high}$ population of MSCs for use according to any one of items 14 to 67, wherein the MSCs and subject are from the same species or genus.

69. The enriched integrin $\alpha10^{high}$ population of MSCs for use according to any one of items 14 to 68, wherein the MSCs and subject are from a different species or genus.

70. The enriched integrin $\alpha10^{high}$ population of MSCs for use according to any one of items 14 to 69, wherein the cells are derived from fetal, neonatal, juvenile or adult MSCs and/or progenitor cells.

71. The enriched integrin $\alpha10^{high}$ population of MSCs for use according to any one of items 14 to 70, wherein the cells are not derived from embryonic cells or from an embryo.

72. The enriched integrin $\alpha10^{high}$ population of MSCs for use according to any one of items 14 to 71, wherein the administration results in increased collagen production, proteoglycan production, and/or lubricin at the site of administration.

73. The enriched integrin $\alpha10^{high}$ population of MSCs for use according to any one of items 14 to 72, further comprising administering an anti-inflammatory agent in combination with the MSCs.

74. The enriched integrin $\alpha10^{high}$ population of MSCs for use according to any one of items 14 to 73, wherein the MSCs do not express MHCII and CD45.

75. The enriched integrin $\alpha10^{high}$ population of MSCs for use according to any one of items 14 to 74, wherein the MSCs express CD44, CD90 and CD105.

76. Use of an enriched integrin $\alpha10^{high}$ population of MSCs, wherein at least 60% of the total cells comprised in the population express integrin $\alpha10$ subunit, and wherein said MSC is selected from the group consisting of a mesenchymal stem cell, a mesenchymal progenitor cell, and a mesenchymal stromal cell, for the preparation of a medicament for the prevention or treatment of degenerative joint disease (DJD), traumatic joint injuries, and/or degenerative disc disease.

77. A method of treating and/or preventing a degenerative joint disease (DJD), traumatic joint injuries, and/or a degenerative disc disease in a subject comprising administering an enriched integrin $\alpha10^{high}$ population of MSCs to a subject at risk for, or having, subchondral bone sclerosis, wherein at least 60% of the cells of the population of MSCs express integrin $\alpha10$ subunit, and wherein said MSC is selected from the group consisting of a mesenchymal stem cell, a mesenchymal progenitor cell, and a mesenchymal stromal cell, thereby treating and/or preventing a degenerative joint disease (DJD), traumatic joint injuries, and/or a degenerative disc disease.

78. The use or method according to any one of items 76 and 77, wherein the DJD is selected from a group consisting of subchondral bone sclerosis, subchondral bone disease, cartilage degeneration, post-traumatic osteoarthritis, inflammatory arthritis, and congenital malformation and/or deformation of the musculoskeletal system.
79. The use or method according of any one of items 76 to 78 wherein the traumatic joint injury comprises sport injuries.
80. The use or method according of any one of items 76 to 79 wherein the traumatic joint injury is selected from a group consisting of osteochondral damage, tendon damage, ligament damage, and muscle damage.
81. The use or method according of any one of items 76 to 80 wherein the osteochondral damage comprises articular cartilage damage and/or bone damage.
82. The use or the method according to any one of items 76 to 81, wherein at least 65%, such as at least 70%, such as at least 75%, such as at least 80%, such as at least 85%, such as at least 90%, such as at least 95%, such as at least 96%, such as at least 97%, such as at least 98%, such as at least 99%, such as at least 100% of the total cells comprised in the population express integrin α10 subunit.
83. The use or the method according to any one of items 76 to 82, wherein the cells are induced to express integrin α10 subunit.
84. The use or the method according to any one of items 76 to 83, wherein the stem cells are derived from adipose tissue, bone marrow, synovial membrane, peripheral blood, cord blood, umbilical cord blood, Wharton's jelly, or amniotic fluid.
85. The use or the method according to any one of items 76 to 84, wherein the MSCs are derived from adipose tissue.
86. The use or the method according to any one of items 76 to 85, wherein the MSCs are derived from bone marrow.
87. The use or the method according to any one of items 76 to 86, wherein the subject has, or previously had, osteochondral damage, damage or an injury to a joint or bone.
88. The use or the method according to any one of items 76 to 87, wherein the osteochondral damage, cartilage damage or injury is a break, sprain, bruise, tear, fracture or rupture.
89. The use or the method according to any one of items 76 to 88, wherein the osteochondral damage, cartilage damage or injury is a cartilage microfracture.
90. The use or the method according to any one of items 76 to 89, wherein the osteochondral damage, cartilage damage or injury is a chondral defect.
91. The use or the method according to any one of items 76 to 90, wherein the osteochondral damage, cartilage damage or injury is a tendon rupture or a ligament rupture.
92. The use or the method according to any one of items 76 to 91, wherein the osteochondral damage, cartilage damage or injury is a bone fracture.
93. The use or the method according to any one of items 76 to 92, wherein the injury is a sports injury.
94. The use or the method according to any one of items 76 to 93, wherein the subject has malalignment of a bone.
95. The use or the method according to any one of items 76 to 94, wherein the osteochondral damage, cartilage damage or injury is the result of wearing a prosthesis.
96. The use or the method according to any one of items 76 to 95, wherein the osteochondral damage, cartilage damage or injury in the joint is in a muscle, tendon, bone, ligament, cartilage, or meniscus.
97. The use or the method according to any one of items 76 to 96, wherein the osteochondral damage, cartilage damage or injury is cartilage fissuring.
98. The use or the method according to any one of items 76 to 97, wherein the use or method prevents post-traumatic osteoarthritis (PTOA) resulting from subchondral bone disease or osteochondral damage.
99. The use or the method according to any one of items 76 to 98, wherein the MSCs are allogeneic or autologous.
100. The use or the method according to any one of items 76 to 99, wherein the MSCs are administered into a joint cavity.
101. The use or the method according to any one of items 76 to 100, wherein the MSCs are administered via injection.
102. The use or the method according to any one of items 76 to 101, wherein the MSCs are administered in a cell suspension with a pharmaceutically acceptable excipient.
103. The use or the method according to any one of items 76 to 102, wherein the MSCs are formulated into a cell aggregate prior to administration.
104. The use or the method according to any one of items 76 to 103, wherein the MSCs are stored in a media comprising dimethyl sulfoxide (DMSO).
105. The use or the method according to any one of items 76 to 104, wherein the MSCs are administered during a surgery to repair a damaged joint or bone.
106. The use or the method according to any one of items 76 to 105, wherein the MSCs are administered at the same time as setting a bone after a break.
107. The use or the method according to any one of items 76 to 106, wherein the subject is a human, horse, pony, ox, donkey, mule, camelid, cat, dog, pig, or cow.
108. The use or the method according to any one of items 76 to 107, wherein the subject is human.
109. The use or the method according to any one of items 76 to 108, wherein the subject is horse.
110. The use or the method according to any one of items 76 to 109, wherein the subject is dog.
111. The use or the method according to any one of items 76 to 110, wherein the MSCs and subject are from the same species or genus.
112. The use or the method according to any one of items 76 to 111, wherein the MSCs and subject are from a different species or genus.
113. The use or the method according to any one of items 76 to 112, wherein the cells are derived from fetal, neonatal, juvenile, or adult MSCs and/or progenitor cells.
114. The use or the method according to any one of items 75 to 113, wherein the cells are not derived from embryonic cells or from an embryo.
115. The use or the method according to any one of items 76 to 114, wherein the administration results in increased collagen production, proteoglycan production, and/or lubricin at the site of administration.
116. The use or the method according to any one of items 76 to 115, further comprising administering an anti-inflammatory agent in combination with the MSCs.
117. The use or the method according to any one of items 76 to 116, wherein the MSCs do not express MHCII and CD45.
118. The use or the method according to any one of items 76 to 117, wherein the MSCs express CD44, CD90 and CD105.
119. A method of manufacturing the enriched integrin α10$^{high}$ population of MSCs according to any one of items 1 to 13, the method comprising, a. isolating a population of stem cells from adipose tissue, bone marrow, synovial membrane, cord blood, Wharton's jelly, or amniotic fluid;
b. culturing the isolated cells in a plastic culture vessel;
c. discarding non-adhered cells;
d. inducing integrin α10 expression by adding culture media, wherein the culture media is a serum-free media or a media comprising mammalian serum, and wherein the culture media comprises platelet lysate and/or platelet lysate components, and/or growth factors;
e. selecting the cells that express integrin α10, and
f. expanding the selected cells, thereby producing an enriched integrin α10$^{high}$ population of MSCs.
120. The method according to item 119, wherein the culture media in step d. comprises the growth factors FGF2 and/or TGFβ.

EXAMPLES

Example 1. Characterization of Equine MSCs

Equine MSCs were isolated from bone marrow (BM) and adipose tissue (AT). BM aspirates and neck adipose tissue were obtained from healthy equine cadavers with permit from the Swedish Board of Agriculture.

BM aspirates were washed in phosphate buffered saline (PBS) and plated onto cell-culture flasks for plastic adherence in DMEM-F12 media (Gibco) supplemented with 10% fetal bovine serum (FBS) (Biological Industries), 50 μg/L fibroblast growth factor (FGF)-2 (Miltenyi) and 100 U/mL Antibiotic-Antimycotic (Gibco) and incubated at 37° C. in a humidified incubator with 4% O2 and 5% $CO_2$. After 24 h, the non-adherent cells were discarded and fresh medium added. At approximately 80% confluence cells were passaged using Accutase (Gibco) and replated for expansion at a density of 104 cells/cm$^2$ in DMEM F-12 media containing 5% human platelet lysate (PL) from Cook Regentec, 50 μg/L FGF-2 and Antibiotic-Antimycotic.

AT from the equine neck was aseptically minced into smaller pieces and washed prior to digestion with 0.1% type 1 collagenase (Sigma-Aldrich) at 37° C. with gentle agitation for 1.5 h. The samples were centrifuged for 5 min at 300×g where after the adipocyte layer and the collagenase supernatant were aspirated. The remaining stromal vascular fraction was washed with DMEM F-12 medium, filtered through a 100 μm cell strainer and seeded into cell culture flasks containing DMEM F-12 supplemented with 10% FBS and Antibiotic-Antimycotic at a plating density of approximately 35 mL adipose tissue per 200 cm$^2$. Cells were incubated at 37° C. in a humidified incubator with 4% O2 and 5% $CO_2$ and after 24 h, the non-adherent cells were discarded and media containing DMEM F-12, 5% PL and Antibiotic-Antimycotic added. Medium was replaced every 2-3 day and cells were harvested at 80% confluence using Accutase and reseeded for expansion at a cell density of 5000 cells/cm$^2$ in DMEM F-12 media containing 5% PL, 50 μg/L FGF-2 and Antibiotic-Antimycotic.

At each passage the MSCs were immunophenotyped by flow cytometry analysis using a panel of cell surface markers: integrin α10β1 (Xintela), CD90 (BD Pharmingen), CD44, CD105, CD45 and MHC class II (AdB Serotec). In brief, 100,000 cells were washed in PBS supplemented with 1% FBS and 0.1% sodium azide followed by incubation with selective antibody. After incubation, cells were washed twice in buffer and acquired using a BD Accuri C6 flow cytometer. At least 20,000 cells were acquired and analyzed. Results are expressed as percentage of positive cells.

Cells were cultured under hypoxia with PL and FGF-2. MSCs are often routinely propagated in medium containing FGF-2 in order to preserve a stem-like phenotype. However, FGF-2 upregulates MHC II on MSCs in culture[21]. Therefore, cultures were initially supplemented with PL only. MSCs isolated from BM or AT and cultured in media containing platelet lysate exhibited good growth characteristics with doubling times of 1.9 days (46 hours) and 1.6 days (38 hours) respectively. Both AT and BM derived cells showed a morphology typical for MSCs.

Figures 1G, 1H:
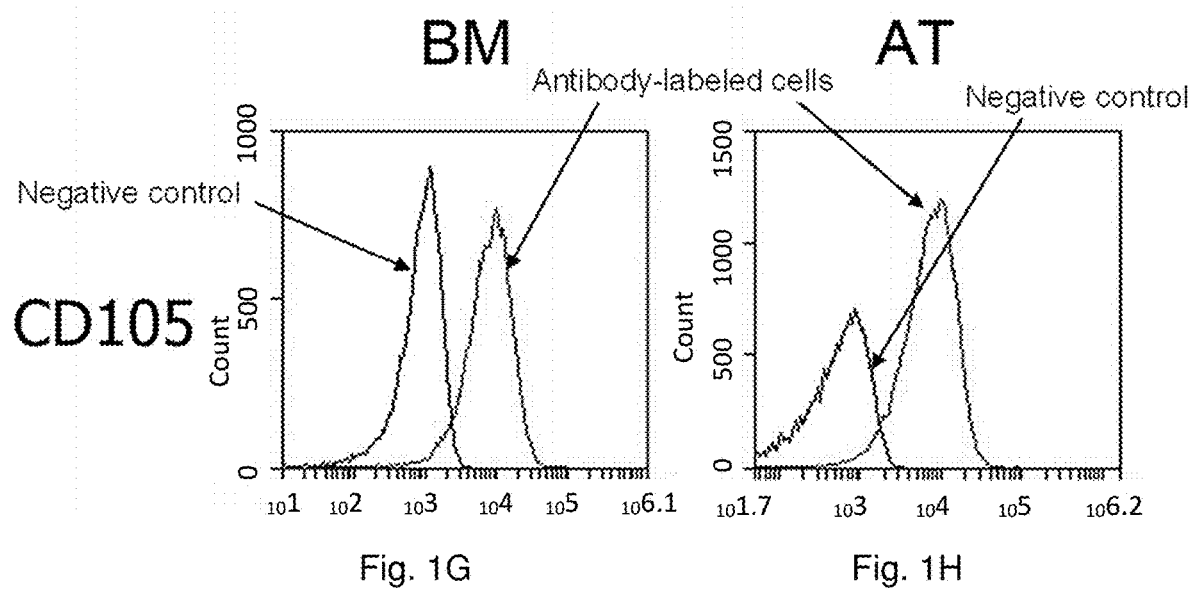
Figures 1I, 1J:
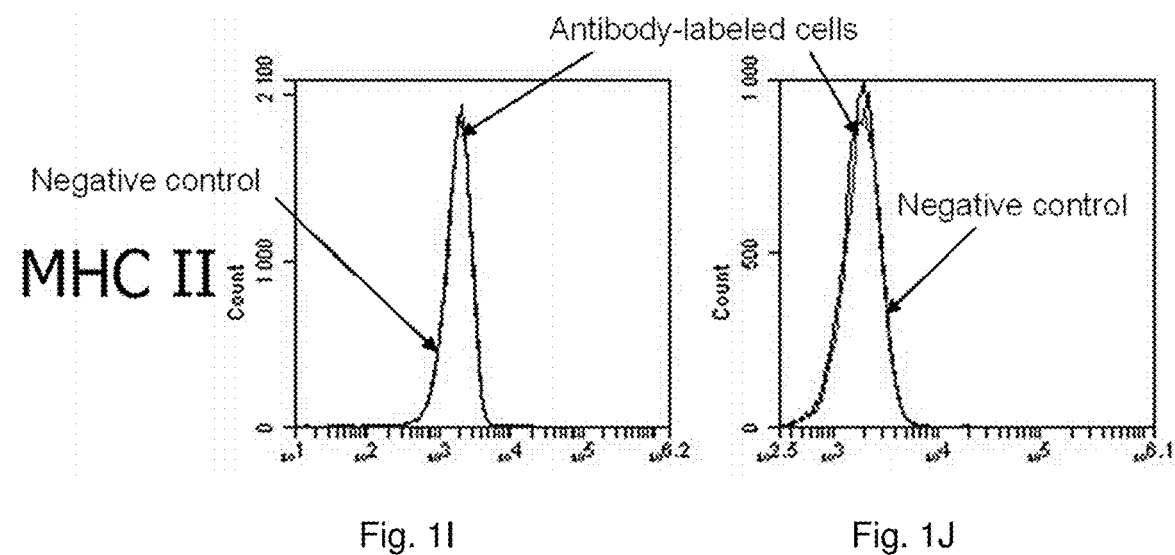

Cells were continuously monitored for expression of integrin α10, CD44, CD45, CD90 and CD105 by flow cytometry. MSCs expressed high levels of the markers CD44, CD90 and CD105 and lacked the hematopoietic cell marker CD45 and MHC class II (HLA-DR) (FIG. 1).

For human MSCs, the cell phenotypes plastic adherence and expression of the surface markers CD73, CD90, and CD105 as well as absence of CD45, CD34, CD14 or CD11b, CD79a or CD19 and HLA-DR surface molecules meets the minimal surface antigen criteria for MSC definition[9]. Due to lack of validated antibodies reacting with equine cell surface markers, expression of CD73, CD34, CD14 or CD11b, CD79a or CD19 were not evaluated. However, both AT- and BM-derived cells adhered to plastic, expressed the tested MSC markers, did not express CD45 or MHC class II and differentiated into chondrocytes.

Conclusion:

AT- and BM-derived cells expressing integrin α10 adhered to plastic, expressed the tested MSC markers (CD44, CD90, and CD105), did not express CD45 or MHC class II and differentiated into chondrocytes.

Example 2. Differentiation of MSCs into Chondrocytes

According to literature, equine MSCs have difficulties differentiating into chondrocytes[16-18]. However, studies with human AT-MSCs show that this could be due to lack of TGFβ-receptors and thus unresponsiveness to the chondrogenic induction signal TGFβ1[9]. This deficiency can be overcome by adding BMP-6 which will stimulate TGFβ-receptor expression in human AT derived MSCs[20]. Integrin α10 expression is up-regulated on human FGF-2-treated MSCs with subsequent improved chondrogenic differentiation potential[15]. Equine AT derived MSCs were primed for chondrogenic differentiation in normal cell culture in fetal bovine serum containing medium and in a medium containing FGF-2. Chondrogenic differentiation was also compared by collagen type II expression in pellet mass cultures after 28 days of incubation in media containing no added growth factors, TGFβ3 only or TGFβ3 and BMP-6 in two different concentrations. Chondrogenic differentiation of equine BM derived MSCs was used for comparison.

Equine AT derived MSCs were cultured and expanded to passage 3 before being subjected to integrin α10 fluorescence-activated cell sorting by FACSAria (BD). The cells were stained using a monoclonal anti-integrin α10 (Xintela) and live cells were sorted into two populations: integrin α10 positive and integrin α10 negative cells. Discrimination of live/dead cells was accompanied by 7-AAD staining (BioLegend). Sorted cells were washed in medium and re-seeded for recovery and expansion one passage before chondrogenic differentiation experiments were performed.

To determine the chondrogenic differentiation capacity of non-sorted and integrin α10 sorted cells, 200,000 MSCs at passage 4 were pelleted in 15 mL polypropylene tubes with chondrogenic medium consisting of DMEM with 4.5 g glucose/L (Gibco) supplemented with 20 μg/L TGFβ3, 20 μg/L BMP-6, 50 mg/L L-ascorbic acid-2-phosphate, 1% Insulin-Transferrin-Selenium (ITS) and 100 nM dexamethasone (Sigma Aldrich). Various growth factor concentrations and combinations of these were tested to optimize equine AT derived MSC chondrogenic differentiation conditions. Medium was changed three times per week and generally maintained for 28 days or as indicated in the chondrogenic time study. Pellets were either embedded in Optimal Cutting Temperature compound (HistoLab) for cryosectioning or snap frozen and stored at −80° C. for RNA extraction. Non-induced chondrogenic pellet mass cultures were used as negative controls in the subsequent immunohistology stainings and PCR experiments.

The pellets were cryosectioned and stained with Alcian Blue for detection of proteoglycans or subjected to immunohistochemical analysis using antibodies directed to the cartilage specific protein collagen type II (Ab3092, Abcam) and integrin α10 (Xintela).

Conclusion:
AT- and BM-derived equine MSCs differentiate into chondrocytes.

Example 3. Levels of Integrin α10 Expression Correlate with Chondrogenic Differentiation Potential Expression of integrin α10β1 on equine MSCs derived from AT and BM was examined. Equine AT derived MSCs were cultured and expanded to passage 3 before being subjected to integrin α10 fluorescence-activated cell sorting by FACSAria (BD). The cells were stained using a monoclonal anti-integrin α10β1 (Xintela) and live cells were sorted into two populations: integrin α10 positive and integrin α10 negative cells.

Discrimination of live/dead cells were accompanied by 7-AAD staining (BioLegend). Sorted cells were washed in medium and re-seeded for recovery and expansion one passage before chondrogenic differentiation experiments were performed.

Flow cytometry analysis of integrin α10 expression revealed that integrin α10 expression was significantly higher in BM derived MSCs compared to AT derived MSCs. Almost 100% of the BM derived MSCs were integrin α10 positive, compared to approximately 30% of the AT derived MSCs (FIG. 2A-B).

Figure 3A:
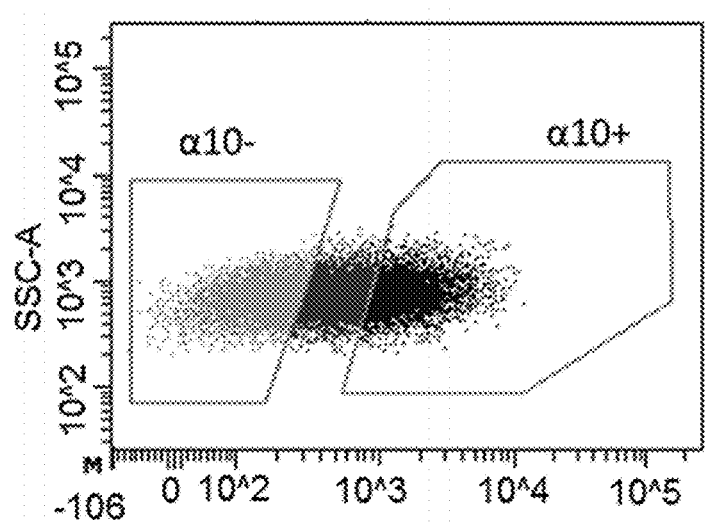
FIG. 3A and FIG. 3B show AT derived MSCs sorted into two distinct cell populations by fluorescence activated cell sorting (FACSAria) using a specific anti-integrin α10 mAb. Integrin α10 labeling intensity was plotted against sidescatter. MSCs gated as integrin $\alpha 10^{high}$ are denoted by blue color (on the right) and MSCs gated as integrin $\alpha 10^{low}$ are denoted by yellow color (on the left) (A). Cells gated as integrin $\alpha 10^{high}$ were subsequently allowed to adhere to plastic and stained with an antibody directed against integrin α10. Cell nuclei were counterstained with DAPI (B).
Figure 3B:
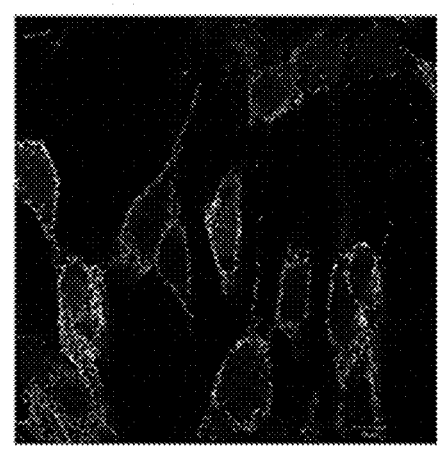
Figure 4A:
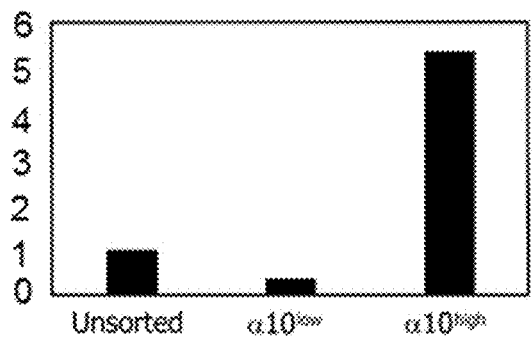
FIG. 4A, FIG. 4B, FIG. 4C, and FIG. 4D show immunohistochemical analysis of pellet mass cultures made on cryosections from unsorted and sorted (integrin $\alpha 10^{high}$ or integrin $\alpha 10^{low}$) AT-MSCs. Cryosections from five differentiation experiments were labeled with anti-type II collagen antibodies and the immunohistochemical color reaction quantified using ImageJ 1.50i software (A). Typical type II collagen expression patterns and levels are shown for cryosections from central regions of pellet mass cultures using unsorted cells (B), sorted integrin $\alpha 10^{high}$ cells (C), or sorted integrin $\alpha 10^{low}$ cells (D). Collagen type II labeling showed intermediate labeling of collagen type II in the unsorted pellets, strong labeling of collagen type II in the sorted integrin $\alpha 10^{high}$ pellets while collagen type II was lower in the integrin $\alpha 10^{low}$ pellets indicating a positive effect of integrin α10 on chondrogenic differentiation.
Figure 4B:
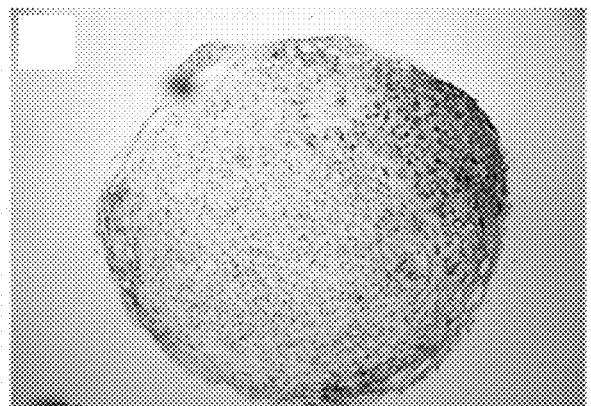
Figure 4C:
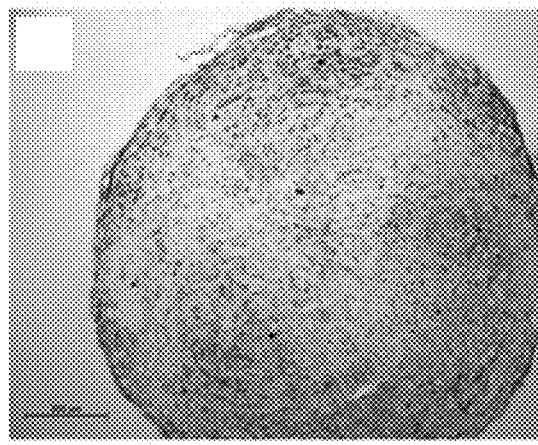
Figure 4D:
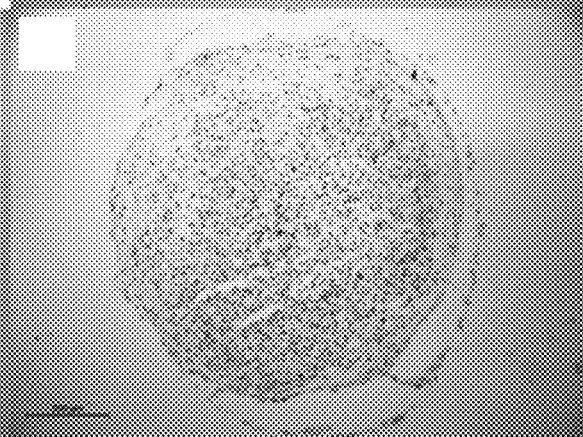

To examine the importance of integrin α10 for chondrogenic differentiation, AT derived MSCs were sorted into two distinct cell populations by fluorescence activated cell sorting (FACSAria) using specific monoclonal antibodies (mAbs) (FIG. 3A). All integrin $α10^{high}$ MSCs expressed integrin α10β1 and expression was localized to the cell surface as shown by immunofluorescence staining (FIG. 3B). The two cell populations, integrin α10 enriched ($α10^{high}$) and α10 depleted ($α10^{low}$), were then expanded and used in pellet mass cultures, where they were compared to unsorted cells. Cells from four equine donors were used. Sorted cells were transferred to pellet mass cultures, differentiated for 28 days, sectioned and analyzed by immunohistochemistry. Immunohistochemical analysis of pellet cryosections showed strong labeling of collagen type II in the pellets made with integrin $α10^{high}$ cells while collagen type II was lower in the integrin $α10^{low}$ pellets (FIGS. 4A-D). Gene expression analysis of pellet mass cultures was made with RNA from unsorted and sorted (($α10^{high}$) or ($α10^{low}$)) AT derived MSCs. GAPDH was used as endogenous control and unsorted cells were used as reference sample for ΔΔCt calculation.

Total RNA was extracted by homogenization of pellets in QIAzol using Precellys lysing kit beads and "homogenisator" followed by RNA isolation according to the RNeasy Lipid Tissue Mini kit (QIAGEN). The RNA was reverse-transcribed into cDNA using a SuperScript VILO kit (Invitrogen). Real-time PCR was conducted using TaqMan assays for the following equine gene transcripts: ACAN, COL1A1, COL2A1, GAPDH, RUNX2, and SOX9 together with the TaqMan Universal Master Mix II according to the protocol in a StepOne Plus Real Time PCR System device (Applied Biosystems). The relative mRNA expression was calculated using the $2^{-ΔΔCt}$ method where GAPDH was the endogenous control (ΔCt) and normalized towards unsorted cells (ΔΔCt)

Figure 5:
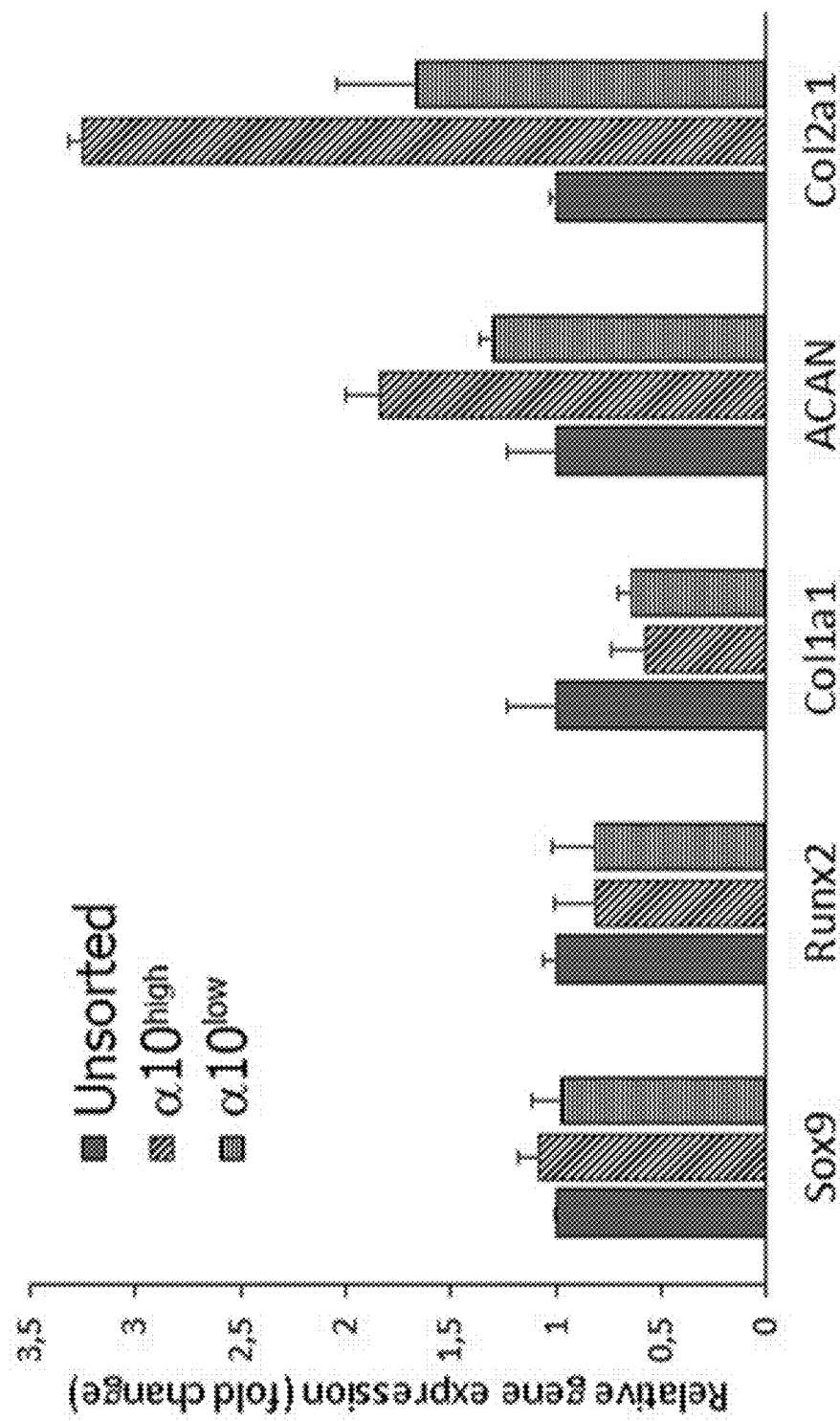
FIG. 5 shows gene expression analysis of pellet mass cultures made with RNA from unsorted and sorted (integrin $\alpha 10^{high}$ or integrin $\alpha 10^{low}$) AT-MSCs. GAPDH was used as endogenous control and unsorted cells were used as reference sample for ΔΔCt calculation. The results show lower expression of type I collagen and higher expression of type II collagen and aggrecan in integrin $\alpha 10^{high}$ pellets compared to integrin $\alpha 10^{low}$ pellets, indicating better chondrogenic differentiation in the pellets from integrin $\alpha 10^{high}$ sorted cells. Bars show mean±SD.
Figure 6A:
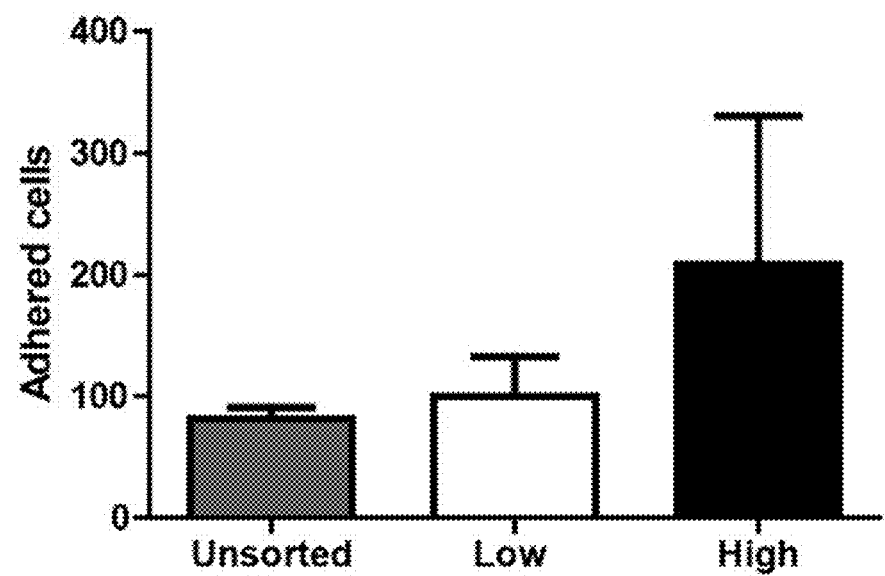
FIG. 6A, FIG. 6B, FIG. 6C, and FIG. 6D show the homing capacity of non-sorted and integrin α10 sorted cells to intact or damaged cartilage. Cells expressing higher levels of integrin α10 ($\alpha 10^{high}$ cells) are better at homing to the region of interest for cartilage repair. Bars represent mean±S.D.
Figure 6B:
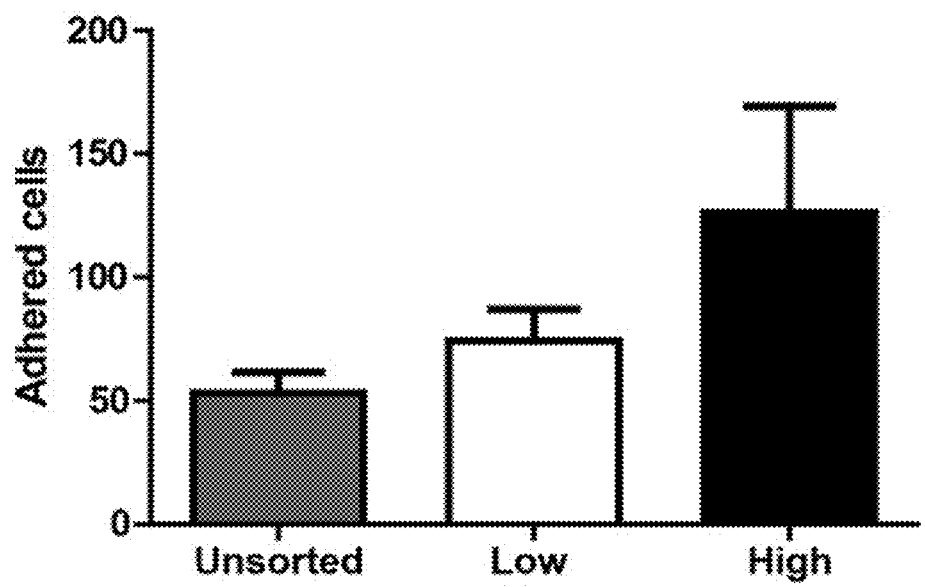
Figure 6C:
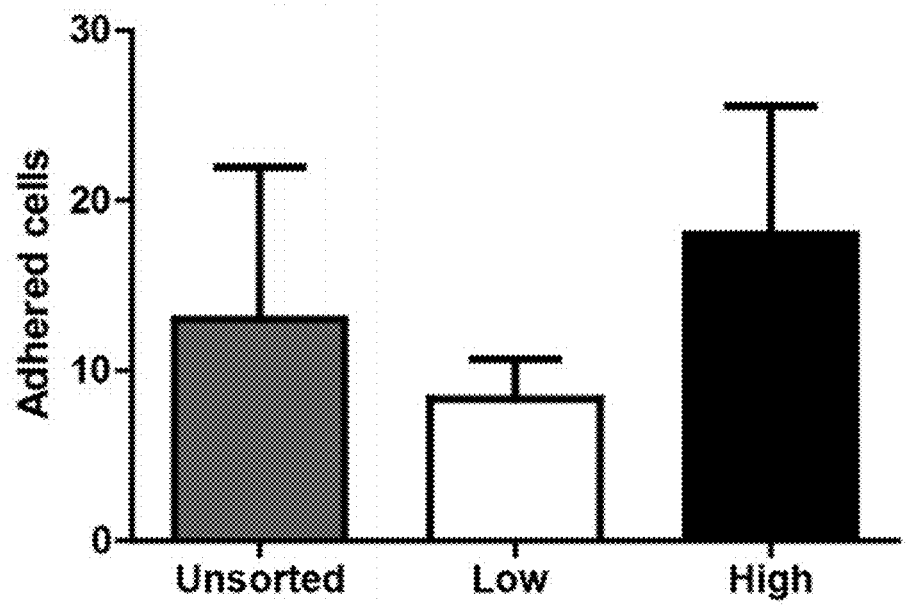
Figure 6D:
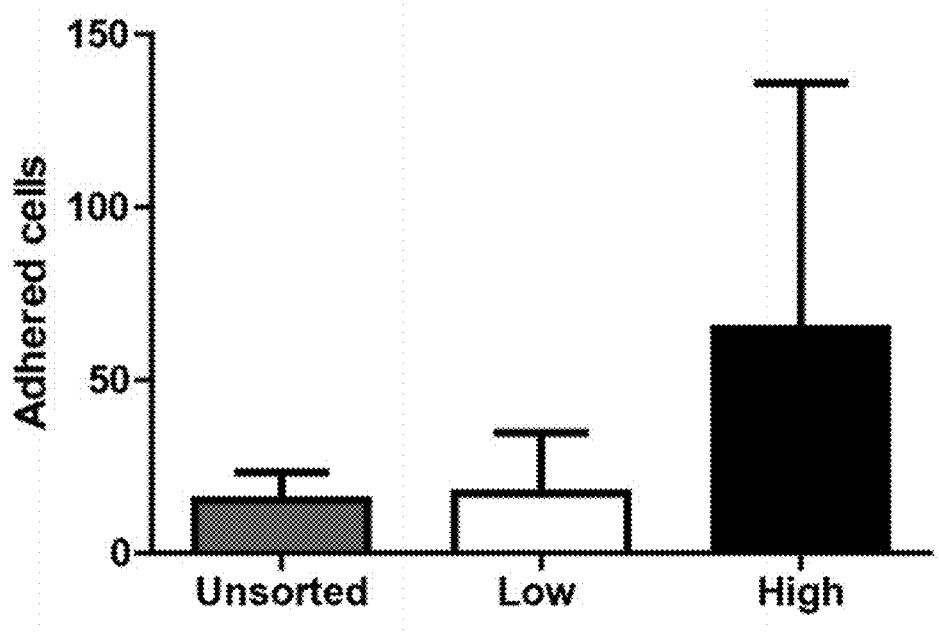

Conclusion: The gene expression results show higher expression of type II collagen and aggrecan in integrin $α10^{high}$ pellets compared to integrin $α10^{low}$ pellets, indicating better chondrogenic differentiation in the pellets from integrin $α10^{high}$ sorted cells (FIG. 5).

Example 4. Levels of Integrin α10 Expression Correlate with Homing Potential

To determine the homing capacity of non-sorted and integrin α10 sorted cells to intact or damaged cartilage, MSCs were incubated for 1 h in rotating plastic tubes with bovine osteochondral explants. These explants were wounded in two locations. One exposing subchondral bone and one with a shallower wound only exposing cartilage. After 1 h adherent cells were counted (with Image J counting cells-plugin) separately for undamaged regions, chondral defects and subchondral defects. Results from two independent experiments are shown in FIG. 6. Integrin $α10^{high}$ cells bound better overall (FIG. 6A), and bound better to intact cartilage (FIG. 6B), chondral defects (FIG. 6C), and subchondral defects (FIG. 6D) than unsorted cells or integrin $α10^{low}$ cells.

Conclusion:
This shows that cells expressing higher levels of integrin α10 ($α10^{high}$ cells) could be better at homing to the region of interest for cartilage repair.

Example 5. Investigation of Integrin α10β1 Positive MSCs in Horses with Post Traumatic Osteoarthritis (PTOA)

This study evaluated the safety and efficacy of integrin α10β1 positive MSCs in an equine PTOA model.

A. Animals and Surgeries

Horses were selected for inclusion in the study based on age (range, 2-5 years). Prior to enrolment, each horse underwent a routine general physical examination and a lameness evaluation to rule out body system abnormalities, particularly musculoskeletal and neurologic abnormalities, which could impact the study. Only horses determined to be sound in the hind limbs and in good general health were enrolled in the study.

Upon arrival, horses were confined to stalls. Clinical parameters were evaluated once pre-operatively, twice daily for 3 days post-operatively, then once daily for 10 days post-operatively. Daily physical exams included vital parameters, mucous membrane color, capillary refill time, gastrointestinal motility, digital pulses, fecal and urine output, appetite, and water intake. Physical exam values were recorded in each horse's individual medical record. Anesthesia was induced, maintained, and monitored, by board certified veterinary Anesthesiologists. Horses were sedated, and then general anesthesia was induced and maintained according to the discretion of the anesthesiologist and in agreement with the study and IACUC protocols. Additional medication or fluid therapy was administered when necessary, at the discretion of the attending anesthesiologist. Following completion of the surgical procedure, horses were placed in lateral recumbency in a padded recovery box. Horses were given additional sedation for recovery. The endotracheal tube was removed once the horse was breathing spontaneously. Horses were monitored continuously during anesthetic recovery and returned to their stall once standing steadily and fully loading all limbs. No significant complications were encountered during induction, general anesthesia, or anesthetic recovery. Anesthetized horses were positioned in dorsal recumbency and both left and right hock joints were clipped. Aseptic preparation of the skin and routine sterile draping were then performed. A standard dorsal approach was made to the hock (talocrural) joint. An 18-gauge needle was placed in the joint and synovial fluid was collected for analysis, as described below. The joint was distended with saline. A 5 mm stab incision was made lateral to the extensor tendon, and the arthroscope was inserted. The joint was explored and needles were used to determine the portal position for introduction of the impactor. The impactor was positioned within the joint so that the tip was perpendicular to the axial surface of the medial trochlear ridge of the talus. Three impacts, spaced approximately 1 cm apart, were applied to the axial aspect of the medial trochlear ridge of the talus. Impact force was recorded during impact by a load cell within the impactor. A synovial membrane biopsy was obtained for histologic analysis. This procedure was repeated on the opposite limb. Arthroscopic video was obtained of all surgeries. The skin incisions were closed using non-absorbable suture material in simple interrupted pattern, the joints were bandaged, and the horse was transported to recovery.

B. Preparation and Injection of Equine Integrin Alpha 10 Selected MSCs

Cells prepared according to Examples 1-3, called Equine integrin alpha10 selected MSCs, hereinafter "Eq12a10+0.1 cells", were utilized in these studies. Eq12a10+0.1 cells were stored in liquid nitrogen until use (four-days post-impact surgery). Vials were thawed, cells were counted, and the viability was assessed using trypan blue. The cells were then centrifuged and resuspended in PBS at a concentration of approximately $6 \times 10^6$ cells/ml. Cells were immediately transferred to the treatment area for injection.

Three ml aliquots of both the cell suspension and control PBS was sterilely drawn into 6 ml syringes through 3-inch, 18-gauge needles. Cells were aspirated slowly, over 20-30 seconds. To prepare for injection, the horse was chemically and physically restrained as necessary, and the dorsomedial pouch of the talocrural joint was aseptically prepped bilaterally. The randomized limb receiving the test article was injected first; a 19-gauge needle was inserted into the dorsomedial compartment of the talocrural joint, synovial fluid was aspirated into a 3-ml syringe, and then the loaded syringe was attached and the solution was emptied at a slow and steady pace (over 3-5 seconds) to deliver more than 1 million cells into the joint cavity. The same procedure was followed for injection of the control PBS into the opposite limb.

Preoperative preparation and anesthesia were carried out as described above for the initial surgeries. Anesthetized horses were positioned in dorsal recumbency and both left and right hock joints were clipped, prepped and draped routinely. A standard dorsal lateral approach was made to the hock joint. An 18-gauge needle was placed in the talocrural joint and synovial fluid was collected for analysis, as described below. The joint was distended with saline. A 5 mm stab incision was made lateral to the extensor tendons for the arthroscopic sleeve. The joint was explored and scored using the ICRS scoring method. A synovial membrane biopsy was obtained for histologic analysis. This procedure was repeated on the opposite limb. The skin incisions were closed using non-absorbable suture material in simple interrupted pattern, the hock joints were bandaged, and the horse was transported to recovery. Post-operative recovery was as described above.

Synovial fluid samples from each talocrural joint were aspirated from all horses immediately prior to the impact surgery and at days 4, 7, 14, 28, 42, 70, 98, 126, 154 post-operatively as well as at euthanasia. At time points other than that of the impact surgery, the test article injection, and the 6 week recheck surgery, horses were chemically and physically restrained as necessary and the dorsomedial pouches of the talocrural joints were aseptically prepped bilaterally. A 19-gauge needle was inserted into the dorsomedial compartment of the talocrural joint and synovial fluid was aspirated into a 3-mL syringe. Approximately 1 mL of the aspirate was submitted to the Cornell University Clinical Pathology Laboratory for a full synovial fluid evaluation (smear and differential counts). The remaining synovial fluid samples were centrifuged to remove the cell pellet, transferred into microcentrifuge tubes and stored in a −80° C. freezer.

At 6 months, horses were sedated and humanely euthanized according to AVMA guidelines with an intravenous overdose of barbiturate (pentobarbital). Joint fluid was collected by sterile methods, and a standard necropsy examination was performed by a board certified veterinary pathologist. Tissue samples of the major organs were collected for histologic examination. Talocrural joints were harvested, tagged for identification and packaged for transport in a cooler. Chain of custody forms remained with the joints at all times.

C. Analyses

Following MRI examination, talocrural joints were dissected and examined. Samples of the synovial membrane were harvested and fixed for histologic processing. India ink was applied to the articular surface, and digital photographs were obtained. India ink contains particulate carbon, and adheres to area of the articular surface where the cartilage integrity is compromised. Osteochondral blocks containing the impact sites as well as non-impacted control cartilage were harvested and fixed for histologic processing.

For each outcome measure of joint health with more than one sampling time (lameness, synovial fluid analysis, synovial fluid ELISA, arthroscopic scores, synovial membrane histology) a mixed effect model was fitted to the data with horse as a random effect, and treatment (control or treatment) and time as fixed effects and an interaction term for treatment*time. Tukey's post hoc and linear contrasts were used as appropriate to test differences between groups of specific interest. A paired t-test was performed on cartilage histology and MRI scores. Statistical analysis was performed using JMP 12 (SAS Institute, Cary, N.C., USA). Significance was set at $p<0.05$.

Model fit for the majority of analyses was fair (adjusted $R^2=0.25-0.50$) or good ($R^2=0.50-0.75$), which are considered acceptable for in vivo animal studies. Model fit was poor (adjusted $R^2=<0.25$) in some instances.

D. Radiograph Results

Summary radiograph data are presented in Table 5.

Baseline (pre-operative) findings: On pre-operative radiographs, all but one horse had radiographically normal hock joints; free of sclerosis, periarticular osteophytes, joint space narrowing, or joint enlargement. One horse had a mild periarticular osteophyte on the dorsomedial surface of the proximal central tarsal bone. This was documented and determined to be inconsequential for study inclusion criteria.

Figure 7:
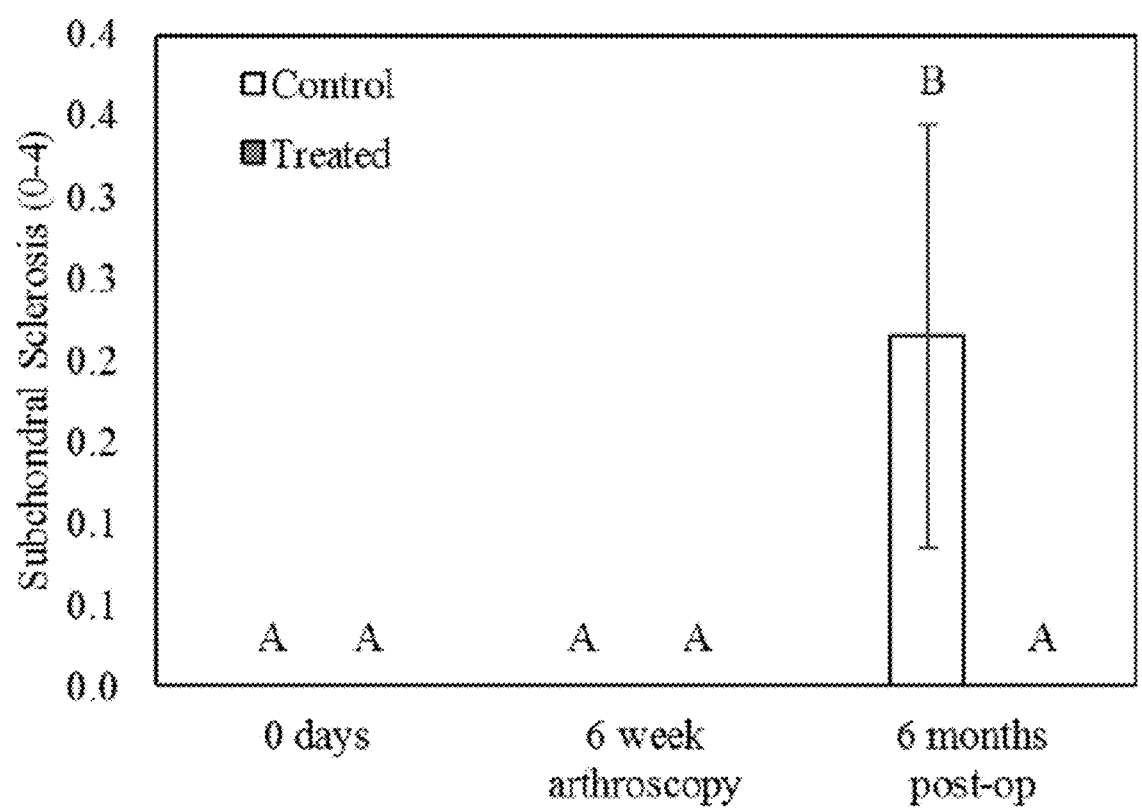
FIG. 7 shows that the subchondral bone sclerosis component score in 6-month control limbs was significantly higher than treated limbs at 6-months and significantly higher than treated or control at 6 weeks and study entry (0 days). Bars represent mean±S.E. Groups that do not share a common letter are significantly different from each other at p<0.05.

Subchondral bone sclerosis: At the 6-month study end, the control group had significantly more sclerosis than the treatment group (FIG. 7; p=0.004; adjusted $R^2$=0.03). Sclerosis is increased bone density which makes the bone harder and less able to absorb and transmit forces away from the articular cartilage. Sclerosis is a hallmark of osteoarthritis and can be either a cause or a result of cartilage deterioration. Because this study is a model system for post-traumatic osteoarthritis, it follows that the increase in subchondral bone sclerosis is a result of joint trauma, verifying that this model induces osteoarthritis. The increase in sclerosis in the control group at study end suggests that the cartilage in the control group would continue to deteriorate over time due to the increased absorption of forces transmitted during weight bearing.

Conclusion:

at the 6-month study endpoint, less radiographic subchondral bone sclerosis was found in the treated limbs compared to controls. Subchondral bone sclerosis would likely result in continued cartilage deterioration and progression of arthritis, and this effect would be expected to be magnified in the face of exercise.

E. Synovial Fluid ELISA Results

Six ELISAs were performed on synovial fluid samples that were obtained from the left and right talocrural joints at time points 0, 4, 7, 14, 28, 42, 70, 98, 126, 154, and 169 days post-operatively. Samples were centrifuged to remove cell debris and stored at −80° C. until analysis. Summary data is presented below in Table 9.

Figure 8:
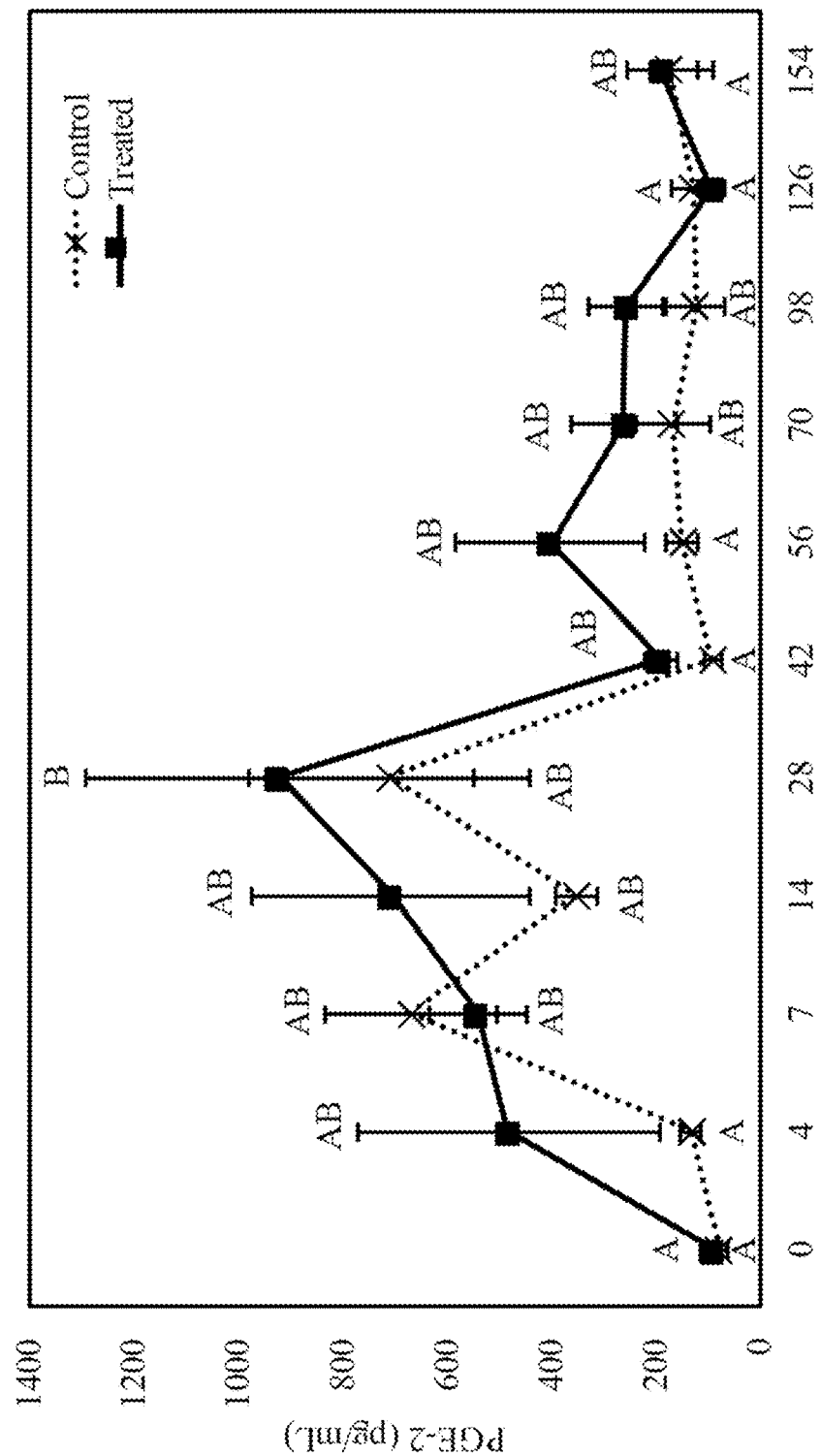
FIG. 8 shows that prostaglandin E2 (PGE-2) levels were greater in treated limbs compared to control limbs at 9/11 time points and significantly greater in treated limbs at 28-days post op compared to control limbs at time 0, 4, 42, 56, 126, and 154 days. Data are presented as mean±S.E. Groups that do not share a common letter are significantly different at p<0.05.

Prostaglandin E2 (PGE-2): MSCs are thought to be immunomodulatory, partially thought upregulation of PGE-2. PGE-2 increased in both treatment and control groups from time 0 to 28 days. It then sharply decreased and remained low, but higher than baseline values throughout the study. PGE-2 concentration was higher in treatment compared to control limbs at 9 of the 11 time points. At 28 days, PGE-2 was significantly increased in treated limbs compared to control at time 0, 4, 42, 56, 126, and 154 days (FIG. 8), suggesting enhanced modulation of the post-operative articular environment in treated compared to control limbs.

Figure 9:
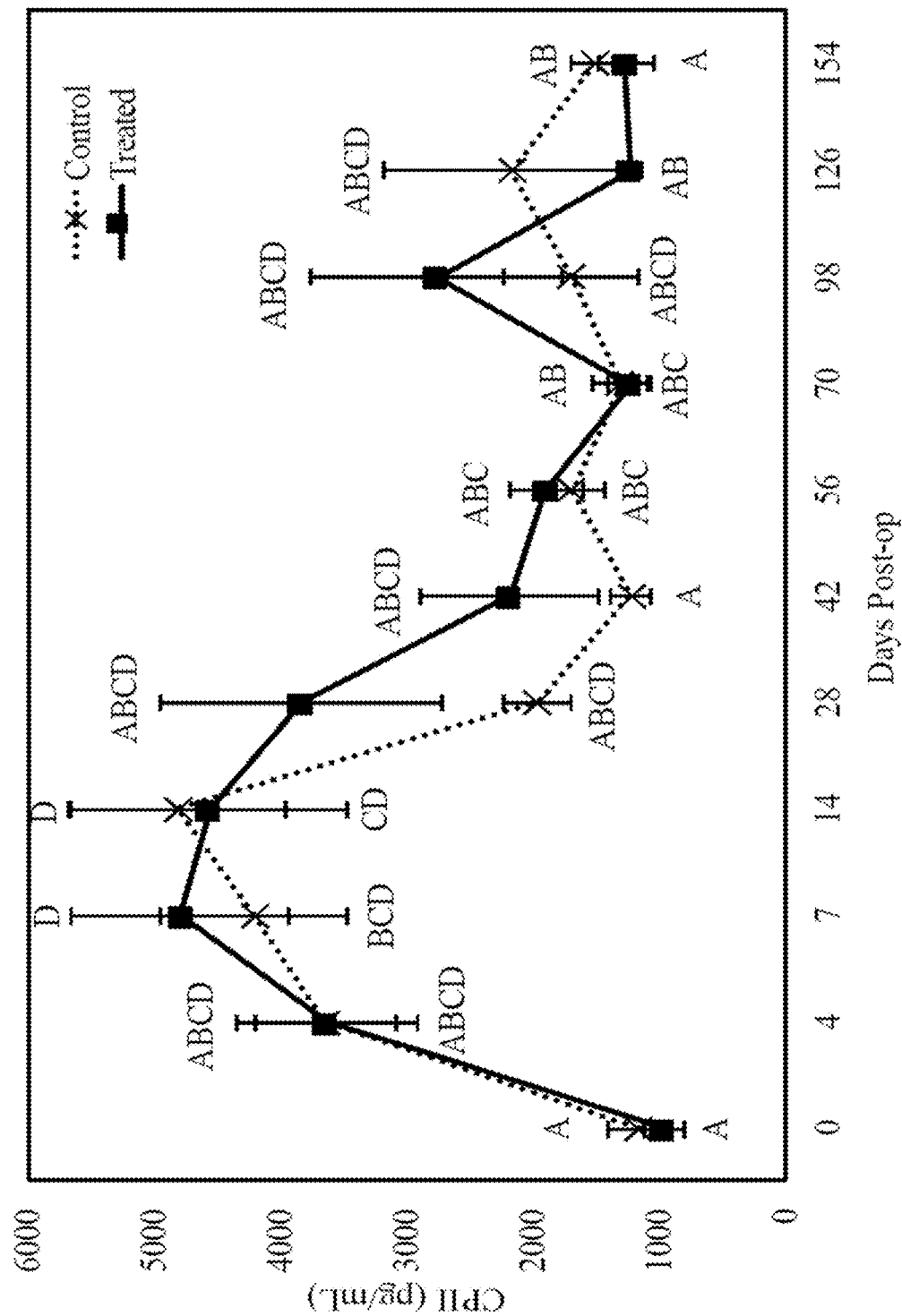
FIG. 9 shows that procollagen II C-propeptide (CPII) levels, indicating increased collagen type II synthesis, were higher in treated compared to control limbs at several time points and significantly greater in treated and control limbs at 7 and 14 days compared to time 0 and study end (day 154). Data are presented as mean±S.E. Groups that do not share a common letter are significantly different at p<0.05.

Collagen CPII: This assay is also known as ProCollagen II C-Propeptide Assay. The CPII assay measures the released carboxy propeptide in the formation of collagen, and therefore reflects changes in the rate of collagen type II synthesis. CPII tended to be greater in synovial fluid from treated limbs compared to control limbs (FIG. 9) suggesting increased type II collagen synthesis in the treated limbs. Both treated and control limbs had increased CPII at 7 and 14 days post-operatively compared to time zero and study end.

Figure 10:
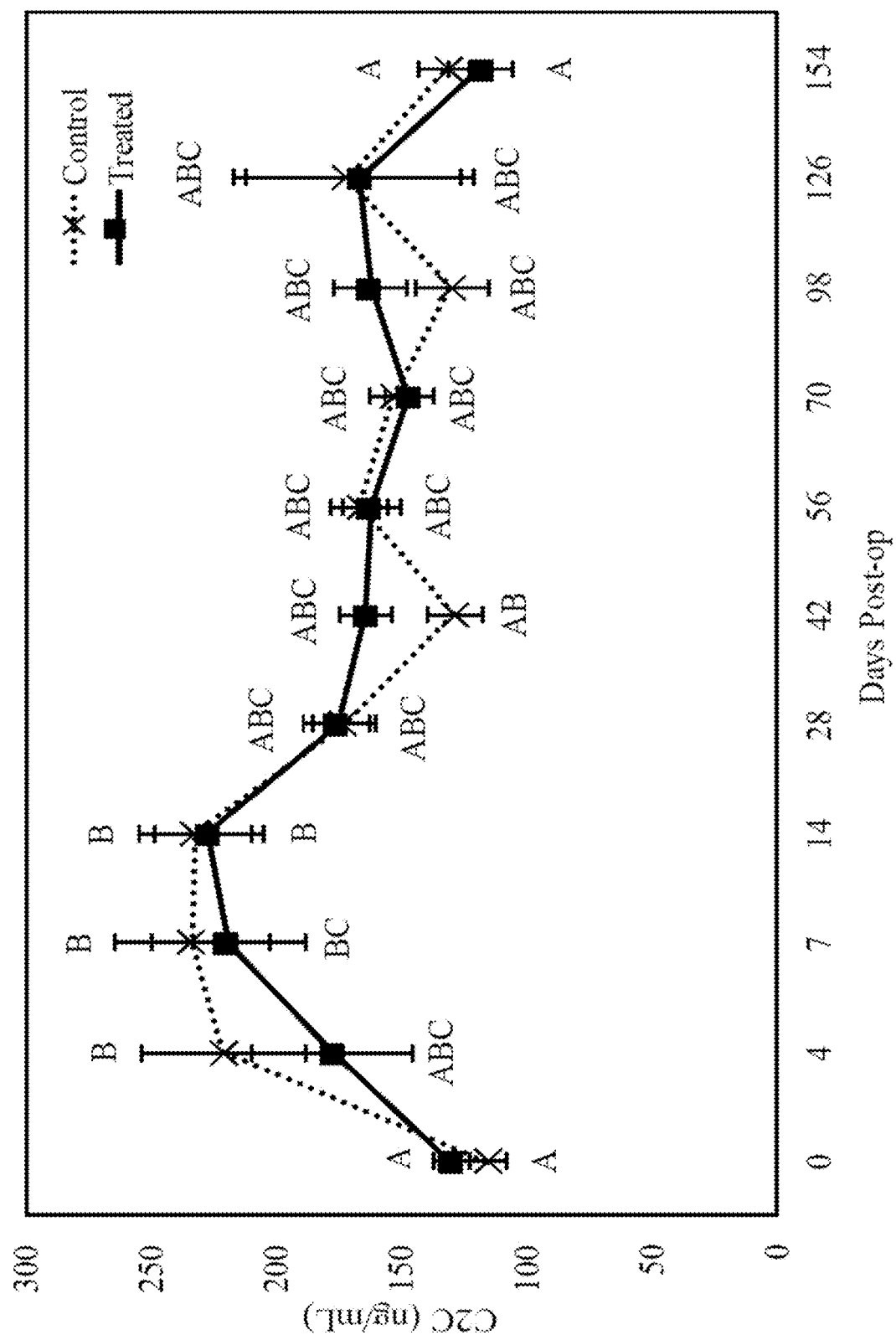
FIG. 10 shows results of the C2C ELISA. The C2C ELISA measures the neoepitope at the C-terminus of 3/4 peptide which is generated through cleavage of type-II collagen by collagenases. In both treated and control groups, C2C significantly increased from the impact surgery through day 14, and then decreased throughout the study to values not different from time 0. Data are presented as mean±S.E. Groups that do not share a common letter are significantly different at p<0.05.

Collagen C2C: This assay measures the neoepitope (at C-terminus of 3/4 peptide) generated through cleavage of type-II collagen by collagenases. C2C concentrations significantly increased in treated and control joints at days 4-14 post operatively (FIG. 10), and then decreased throughout the study to values not significantly different from time 0. Like TNF-α, this support the model as one of mild post-traumatic osteoarthritis.

F. Cartilage Histology Results

All H&E and Safranin-O fast green stained osteochondral slides were scored by consensus of investigators, who were blinded to treatment group while scoring. Data are presented in FIG. 11 with summary data in Table 11. For all horses two non-impacted areas of cartilage were examined in each joint; the lateral trochlear ridge of the talus, and the distal intermediate ridge of the tibia, which is the opposing joint surface that articulates with the impacted region on the medial trochlear ridge. Both samples were examined, then a single score was assigned for non-impacted cartilage. For all horses, focal regions of the medial trochlear ridge containing each of the three impacts were examined, then a single score was assigned for impacted cartilage for each joint.

General Observations—Impacted Cartilage: As expected, all impacted areas of cartilage had moderately to severely abnormal cartilage scores.

Total Joint Scores: The results show that MSC treatment led to significantly better score for fissuring/fibrillation. All other component scores as well as the total score were also better in the treated group (Table 11) as compared to control.

Figure 12:
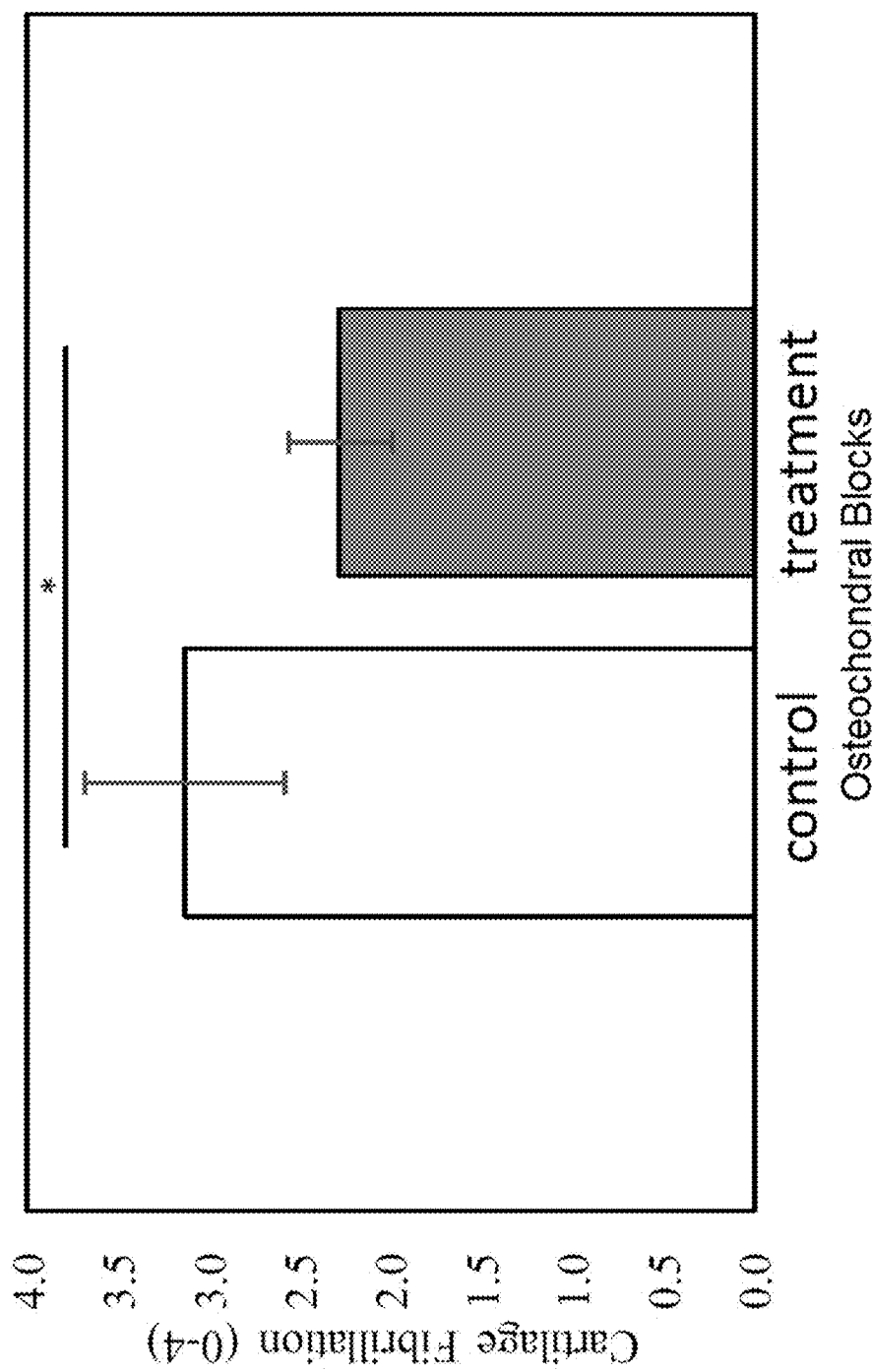
FIG. 12 shows that cartilage fibrillation was significantly less (better) in treated limbs at study end (6-months) compared to control limbs. Bars represent mean±S.E., p<0.039, paired-t-test, one-tailed.

Cartilage Fissuring/Fibrillation: Treated joints has a significantly lower (better) score for fibrillation/fissuring (FIG. 12, p=0.039, one-tailed t-test) and for delta fibrillation/fissuring (p=0.030, one-tailed t-test). This finding demonstrates that treated joints had less structural damage in areas of injury than controls.

Additional Observations: Cartilage clefts were noted to be healed in several slides, subjectively more often in treated limbs. This healing-type response has not been previously noted in this animal model of post traumatic osteoarthritis. Subchondral bone sclerosis can be observed in numerous slides as well.

TABLE 11

Osteochondral histology component and total scores. Data represent mean ± S.E.

| Limb | Cell cluster/ chondrone formation | Fibrillation/ fissuring of cartilage | Focal cell loss | GAG loss | Total joint score |
| --- | --- | --- | --- | --- | --- |
| Control | 3.57 ± 0.30 | 3.14 ± 0.55 | 3.00 ± 0.44 | 3.28 ± 0.36 | 13.00 ± 1.15 |
| Treatment | 3.14 ± 0.34 | 2.29 ± 0.29 | 2.57 ± 0.37 | 3.14 ± 0.34 | 11.14 ± 1.09 |

F. Osteochondral Immunohistochemistry (Collagen Type I and II) Results

Figure 11A:
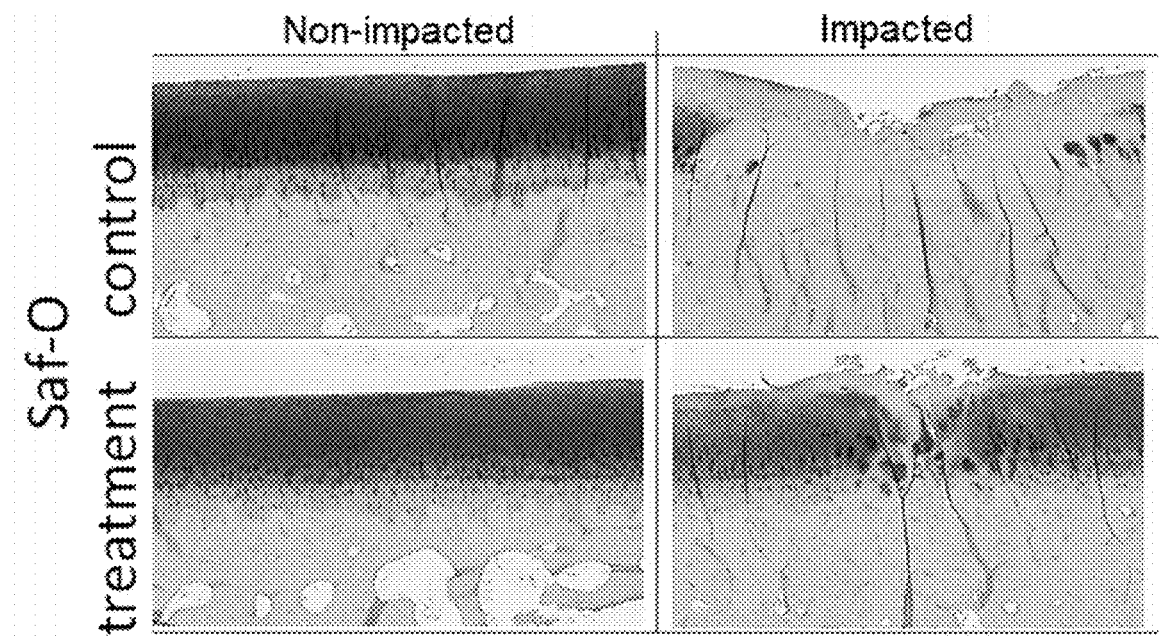
FIG. 11A and FIG. 11B show histology of osteochondral sections. Talocrural (hock) joints were prepared for histology and sections were stained with Safranin-O/Fast Green (A). Normal levels of proteoglycans could be seen in non-impacted areas of the cartilage both in treatment and control limbs. At impacted areas, differences in proteoglycan content and chondrocyte organization could be seen in some horses. Adjacent, sections were labeled with antibodies directed against type II collagen (B). Normal levels of type II collagen could be seen in non-impacted areas of the cartilage both in treatment and control limbs. At impacted areas differences in type II collagen content and expression pattern could be seen in some horses.
Figure 11B:
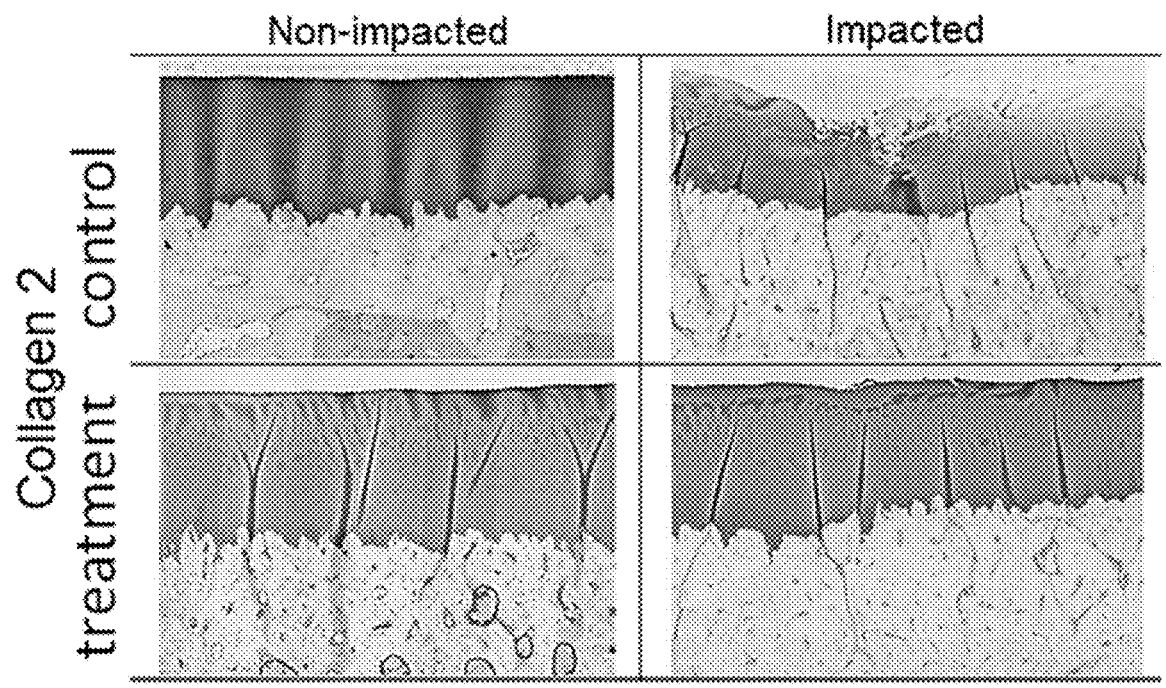
Figure 13:
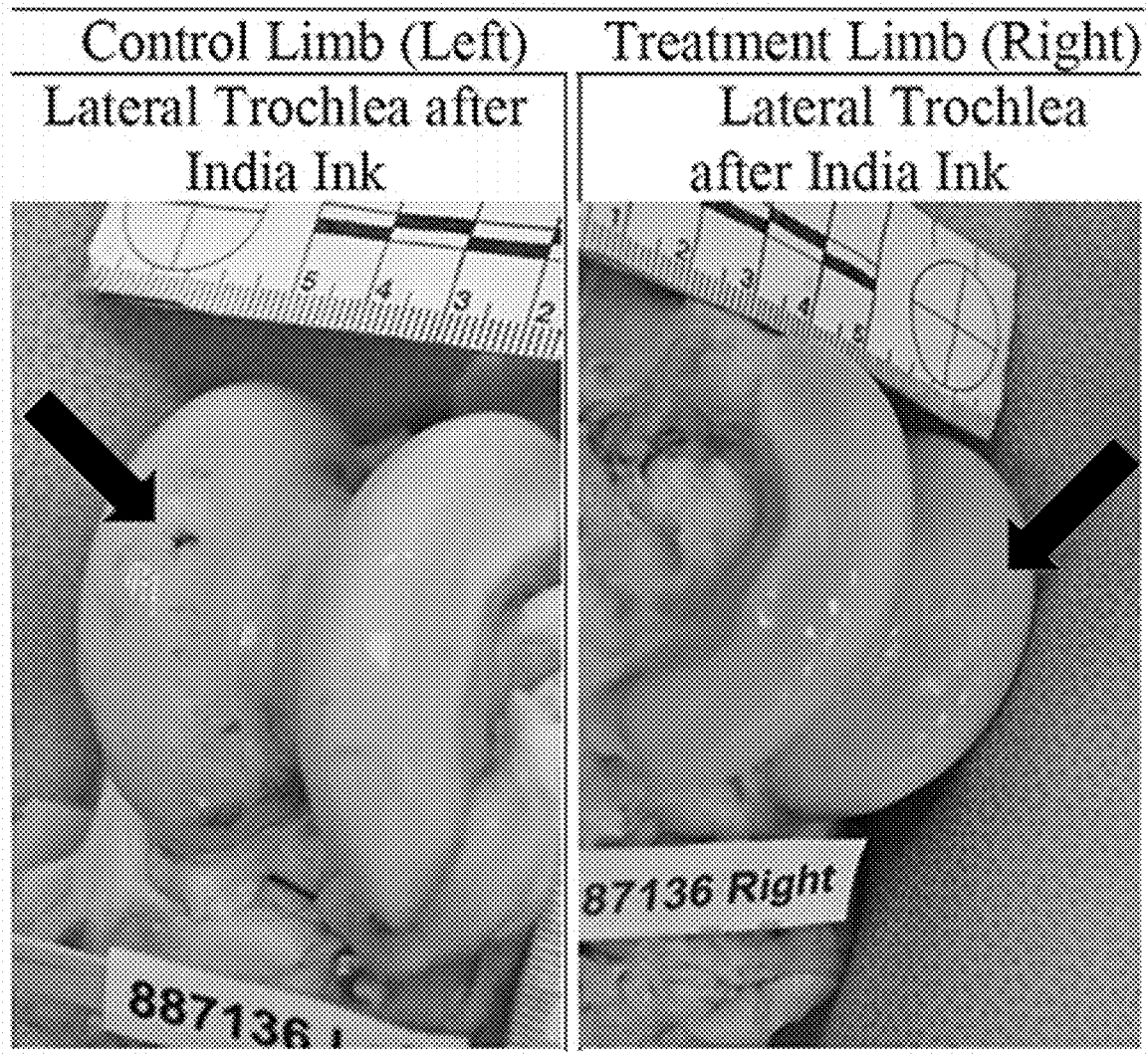
FIG. 13 shows India ink staining. Post mortem, India ink was applied to the articular surface, and digital photographs were obtained. India ink contains particulate carbon, and adheres to area of the articular surface where the cartilage integrity is compromised. Arrows point to impact areas where India ink adhesion can be seen as a black stain on damaged cartilage. More India ink adhered to control limb cartilage surfaces than to treatment limb cartilage surfaces indicating a beneficial effect of the treatment.

Immunohistochemisty for collagens type I and II was performed on osteochondral sections (FIG. 11). India ink staining was also performed (FIG. 13). No quantitative assessment of the immunohistochemistry sections was performed due to the inherently high variability in the assay.

Collagen Type I—Non-impacted (remote) cartilage: Immunohistochemistry for collagen type I was largely unremarkable in the remote control samples in both the treated and untreated control limbs with no collagen type I staining of the articular cartilage.

Collagen Type I—Impacted cartilage: Staining for collagen type I was confined to regions of impact and generally extended 1/4-1/2 into the articular cartilage surface. There were very few changes and no observed differences between treatment and control limbs. In regions of repair tissue (noted above in "Additional Subjective Observations", staining was only noted in the deeper 1/2 of the repair tissue).

Collagen Type II—Non-impacted (remote) cartilage: Immunohistochemistry for collagen type II was largely unremarkable in the control samples with even distribution of collagen type II throughout the cartilage.

Collagen Type II—Impacted cartilage: There were few areas of collagen type II loss in control or treated joints. In the immediate region of the impacts, there was slightly reduced staining for collagen type II. Similar to collagen type I, areas of fibrous repair only stained for collagen type II in the deeper layers of the repair tissue.

Immunomodulatory Chemokines: The most MSC-specific finding in the study was the increased PGE-2 concentration in Eq12a10+0.1 MSCs treated joints compared to controls. PGE-2 modulates chemokines and chemotaxis of pro-inflammatory cells and is therefore a key mediator of immunopathology. All cells are capable of producing PGE-2, and MSCs are known to increase the expression of PGE-2 by myeloid and stromal cells. In this study, PGE-2 concentration in synovial fluid peaked at day 28 and then decreased for the remainder of the study.

Figure 14:
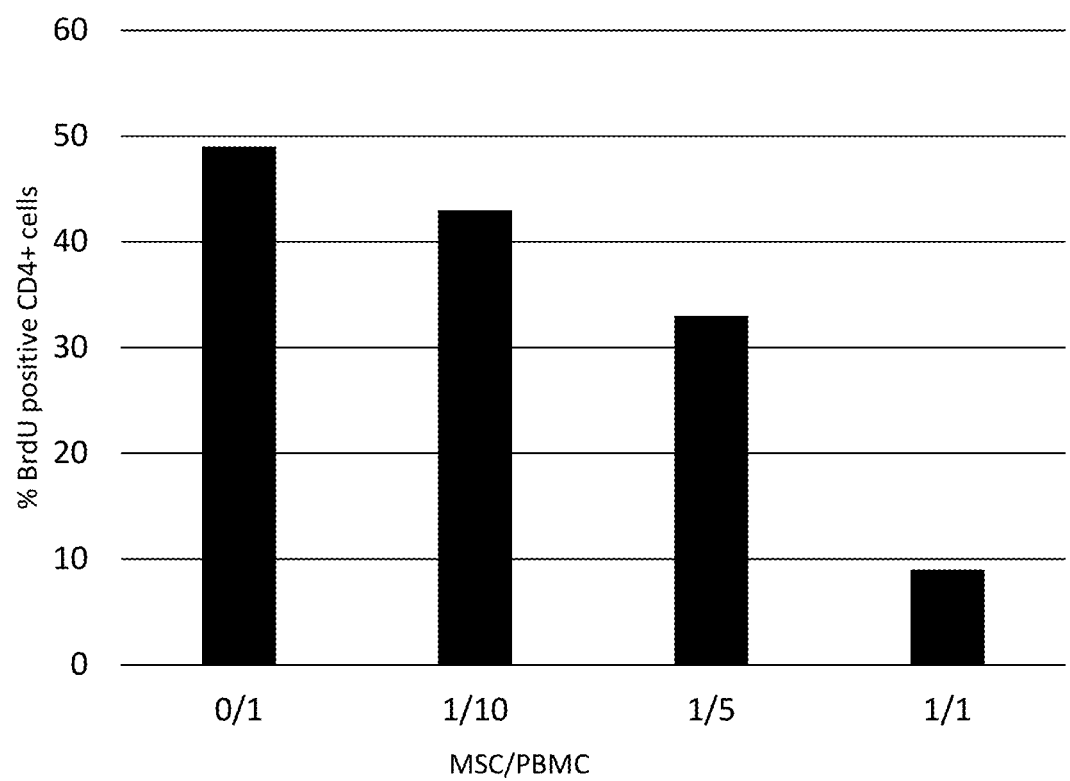
FIG. 14: Immunosuppression assay showing equine integrin α10 selected MSCs isolated from adipose tissue have an immunomodulatory capacity on T cells, demonstrated as a decrease in lymphocyte proliferation with increasing ratios of MSCs to PBMCs. The greatest immunosuppressive effect was generated at one MSC to one PBMC ratio.

Conclusion:

This pre-clinical study supports the use of Eq12a10+0.1 MSCs for the treatment of post-traumatic osteoarthritis. The treatment is safe and there is strong evidence to suggest it may be efficacious in mitigating the effects of joint trauma. For example, cartilage clefts were noted to be healed in several slides, subjectively more often in treated limbs. This healing-type response has not been previously noted in this animal model of post traumatic osteoarthritis Example 6. Immunosuppression The immunosuppression capacity of equine integrin $\alpha 10$ selected MSCs isolated from adipose tissue was also tested. The immunosuppression assay was conducted by having peripheral blood mononuclear cells (PBMC) stimulated with Concanavalin A for 72 hours in co-cultures with allogenic MSCs at different ratios. Lymphocyte proliferation was measured by adding bromodeoxyuridine (BrdU) 24 hours before flow cytometry analysis of the BrdU incorporation to measure of lymphocyte proliferation. Shown in FIG. 14 is the frequency of BrdU positive CD4 expressing T cells.

Conclusion:

equine integrin $\alpha 10$ selected MSCs isolated from adipose tissue have an immunomodulatory capacity on T cells, demonstrated as a decrease in lymphocyte proliferation with increasing ratios of MSCs to PBMCs. The greatest immunosupressive effect was generated at one MSC to one PBMC ratio.

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

REFERENCES

1. Houard X, Goldring M B, Berenbaum F. Homeostatic Mechanisms in Articular Cartilage and Role of Inflammation in Osteoarthritis. Current rheumatology reports. 2013; 15(11):375. doi:10.1007/s11926-013-0375-6.
2. Gelber A C, Hochberg M C, Mead L A, Wang N Y, Wigley F M, Klag M J. (2000). Joint injury in young adults and risk for subsequent knee and hip osteoarthritis. Ann Intern Med. 133, 321-328.
3. Kidd, J. A., Fuller, C. and Barr, A. R. S. (2001). Osteoarthritis in the horse. Equine Veterinary Education, 13: 160-168. doi:10.1111/j.2042-3292.2001.tb00082.x
4. McIlwraith C W, Fortier L A, Frisbie D D, Nixon A J. (2011). Equine Models of Articular Cartilage Repair. Cartilage 2, 317-326. doi: 10.1177/1947603511406531.
5. Goodrich L R, Nixon A J. (2006). Medical treatment of osteoarthritis in the horse—a review. Vet J. 171, 51-69. doi: 10.1016/j.tvjl.2004.07.008
6. Bornes T D, Adesida A B, and Jomha N M (2014). Mesenchymal stem cells in the treatment of traumatic articular cartilage defects: a comprehensive review. Arthritis Research & Therapy 16, 432-451.
7. Mundra V et al. (2013). Mesenchymal stem cell-based therapy. Mol Pharm 2013, 10, 77-89.
8. Raynaud C M and Rafij A. (2013). The Necessity of a Systematic Approach for the Use of MSCs in the Clinical Setting. Stem Cells International 2013, 1-10.
9. Dominici M, Le Blanc K, Mueller I, Slaper-Cortenbach I, Marini F, Krause D et al. (2006). Minimal criteria for defining multipotent mesenchymal stromal cells. The International Society for Cellular Therapy position statement. Cytotherapy. 8, 315-317.
10. Fortier L A, Travis A J (2011). Stem cells in veterinary medicine. Stem Cell Res Ther. 2011 Feb. 23; 2(1):9. doi: 10.1186/scrt50.
11. Samsonraj, R. M., Rai, B., Sathiyanathan, P., Puan, K. J., Rotzschke, O., Hui, J. H., Raghunath, M., Stanton, L. W., Nurcombe, V. and Cool, S. M. (2015), Establishing Criteria for Human Mesenchymal Stem Cell Potency. Stem Cells, 33: 1878-1891. doi:10.1002/stem.1982
12. Lundgren-Akerlund E, Aszòdi A (2014). Integrin $\alpha 10 \beta 1$: a collagen receptor critical in skeletal development. Adv Exp Med Biol 819, 61-71.
13. Gouttenoire J, Bougault C, Aubert-Foucher E, Perrier E, Ronziere M C, Sandell L, et al. (2010). BMP-2 and TGF-beta1 differentially control expression of type II procollagen and $\alpha 10$ and alpha11 integrins in mouse chondrocytes. Eur J Cell Biol 89, 307-314.
14. Gigout A, Jolicoeur M, Nelea M, Raynal N, Farndale R, Buschmann M D (2008). Chondrocyte aggregation in suspension culture is GFOGER-GPP- and beta1 integrin-dependent. J Biol Chem 283, 31522-31530.
15. Varas L, Ohlsson L B, Honeth G, Olsson A, Bengtsson T, Wiberg C, Bockermann R, Jarnum S, Richter J, Pennington D, Johnstone B, Lundgren-Akerlund E, Kjellman C (2007). A10 integrin expression is up-regulated on fibroblast growth factor-2-treated mesenchymal stem cells with improved chondrogenic differentiation potential. Stem Cells Dev 16, 965-978.
16. Vidal M A, Robinson S O, Lopez M J, et al. (2008) Comparison of Chondrogenic Potential in Equine Mesenchymal Stromal Cells Derived from Adipose Tissue and Bone Marrow. Veterinary surgery 37, 713-724. doi: 10.1111/j.1532-950X.2008.00462.x.
17. Kisiday, J. D., Kopesky, P. W., Evans, C. H., Grodzinsky, A. J., McIlwraith, C. W. and Frisbie, D. D. (2008), Evaluation of adult equine bone marrow- and adipose-derived progenitor cell chondrogenesis in hydrogel cultures. J. Orthop. Res., 26, 322-331. doi:10.1002/jor.20508
18. Burk J, Ribitsch I, Gittel C, Juelke H, Kasper C, Staszyk C, Brehm W. (2013). Growth and differentiation characteristics of equine mesenchymal stromal cells derived from different sources. Vet J. 195, 98-106. doi: 10.1016/j.tvjl.2012.06.004. Epub 2012 Jul. 26.
19. Hennig T, Lorenz H, Thiel A, Goetzke K, Dickhut A, Geiger F, Richter W (2007). Reduced chondrogenic potential of adipose tissue derived stromal cells correlates with an altered TGFbeta preceptor and BMP profile and is overcome by BMP-6. J Cell Physiol. 211, 682-691.
20. Estes B T, Wu A W, Guilak F (2006). Potent induction of chondrocytic differentiation of human adipose-derived adult stem cells by bone morphogenetic protein 6. Arthritis Rheum. 54, 1222-1232.
21. Bocelli-Tyndall C, Zaiac P., Di Maggio N., Trella E., Benvenuto F., Iezzi G., et al. (2010). Fibroblast growth factor 2 and platelet-derived growth factor, but not platelet lysate, induce proliferation-dependent, functional class II major histocompatibility complex antigen in human mesenchymal stem cells. Arthritis Rheum. 62, 3815-3825.
22. Su X, Zuo W, Wu Z, Chen J, Wu N, Ma P, et al. (2015). CD146 as a new marker for an increased chondroprogenitor cell sub-population in the later stages of osteoarthritis. J Orthop Res. 33, 84-91.
23. Schrobback K, Wrobel J, Hutmacher D W, Woodfield T B, Klein T J. (2013). Stage-specific embryonic antigen-4 is not a marker for chondrogenic and osteogenic potential in cultured chondrocytes and mesenchymal progenitor cells. Tissue Eng Part A. 19, 1316-1326.
24. Tallone T, Realini C, Bohmler A, Kornfeld C, Vassalli G, Moccetti T et al. (2011). Adult human adipose tissue contains several types of multipotent cells. J Cardiovasc Transl Res. 4, 200-210.

The invention claimed is:

1. A method of treating subchondral bone sclerosis, traumatic joint injuries, and/or degenerative joint disease (DJD) in a mammal in need thereof, comprising injecting a therapeutically effective amount of an autologous or allogenic enriched integrin α10 population of undifferentiated cells into a damaged joint and/or bone of the mammal, wherein at least 60% of the cells of the population express integrin α10 subunit, wherein the cells are WWII negative and CD45 negative, and wherein the cells are selected from mesenchymal stem cells (MSCs), mesenchymal progenitor cells, and mesenchymal stromal cells.

2. The method of claim 1, wherein the degenerative joint disease (DJD) is selected from subchondral bone disease, cartilage degeneration, post-traumatic osteoarthritis, inflammatory arthritis, and congenital malformation and/or deformation of the musculoskeletal system, and wherein the traumatic joint injury is selected from osteochondral damage, tendon damage, ligament damage, and muscle damage.

3. The method of claim 2, wherein the osteochondral damage comprises articular cartilage damage and/or bone damage.

4. The method of claim 2, wherein the osteochondral damage, cartilage damage or injury is a break, sprain, bruise, tear, fracture, rupture, a cartilage fissure, a cartilage microfracture, a chondral defect, a tendon rupture, a ligament rupture, or a bone fracture, and/or wherein the osteochondral damage, cartilage damage or injury in the joint is in a muscle, tendon, bone, ligament, cartilage, or meniscus.

5. The method of claim 1, wherein the population of cells comprise MSCs that are formulated into a cell aggregate prior to intra-articular injection.

6. The method of claim 1, wherein the mammal is a human, horse, pony, ox, donkey, mule, camelid, cat, dog, pig, or cow.

7. The method according to claim 1, wherein at least 65%, at least 70%, at least 75%, at least 80%, at least 85%, at least 90%, at least 95%, at least 96%, at least 97%, at least 98%, at least 99%, 100% of the total cells comprised in the enriched integrin α10 population express integrin α10 subunit.

8. The method according to claim 1, wherein said enriched integrin α10 population is an in vitro cell culture.

9. The method according to claim 1, wherein the cells that express integrin α10 are isolated with an anti-integrin α10 antibody.

10. The method according to claim 9, wherein the anti-integrin α10 antibody is a monoclonal antibody.

11. The method according to claim 1, wherein the cells are derived from adipose tissue, bone marrow, synovial membrane, peripheral blood, cord blood, umbilical cord blood, Wharton's jelly, or amniotic fluid.

12. The method according to claim 1, wherein the cells express CD44, CD90 and CD105.

13. A method of promoting or inducing fracture healing in a mammal in need thereof, said method comprising injecting a therapeutically effective amount of an autologous or allogenic enriched integrin α10 population of undifferentiated cells into a damaged joint and/or bone of the mammal, wherein at least 60% of the cells of the population express integrin α10 subunit, wherein the cells are WWII negative and CD45 negative, and wherein the cells are selected from mesenchymal stem cells (MSCs), mesenchymal progenitor cells, and mesenchymal stromal cells.

14. The method according to claim 13, wherein said enriched integrin α10 population is an in vitro cell culture.

15. The method according to claim 13, wherein the cells that express integrin α10 are isolated with an anti-integrin α10 antibody.

16. The method according to claim 15, wherein the anti-integrin α10 antibody is a monoclonal antibody.

17. The method of claim 13, wherein the population of cells comprise MSCs that are formulated into a cell aggregate prior to intra-articular injection.

18. The method of claim 13, wherein the mammal is a human, horse, pony, ox, donkey, mule, camelid, cat, dog, pig, or cow.

* * * * *

UNITED STATES PATENT AND TRADEMARK OFFICE
CERTIFICATE OF CORRECTION

| | |
|---|---|
| PATENT NO. | : 11,517,593 B2 |
| APPLICATION NO. | : 16/519179 |
| DATED | : December 6, 2022 |
| INVENTOR(S) | : Evy Lundgren Åkerlund, Christina Uvebrant and Jan Talts |

It is certified that error appears in the above-identified patent and that said Letters Patent is hereby corrected as shown below:

In the Claims

Column 31, Claim 1, Line 61, delete "subunit, wherein the cells are WWII negative and CD45" and insert -- subunit, wherein the cells are MHCII negative and CD45 --

Column 32, Claim 8, Line 30, delete "enriched integrin α10 population is an in vitro cell culture." and insert -- enriched integrin α10 population is an *in vitro* cell culture. --

Column 32, Claim 13, Line 48, delete "integrin α10 subunit, wherein the cells are WWII negative" and insert -- integrin α10 subunit, wherein the cells are MHCII negative --

Column 32, Claim 14, Line 53, delete "enriched integrin α10 population is an in vitro cell culture." and insert -- enriched integrin α10 population is an *in vitro* cell culture. --

Signed and Sealed this
Thirty-first Day of January, 2023

Katherine Kelly Vidal
*Director of the United States Patent and Trademark Office*